(12) United States Patent
D'Andrea et al.

(10) Patent No.: US 7,858,331 B2
(45) Date of Patent: Dec. 28, 2010

(54) COMPOSITIONS AND METHODS FOR THE TREATMENT OF CANCER

(75) Inventors: Alan D. D'Andrea, Winchester, MA (US); Toshiyasu Taniguchi, Seattle, WA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 112 days.

(21) Appl. No.: 11/441,289

(22) Filed: May 24, 2006

(65) Prior Publication Data

US 2007/0105130 A1 May 10, 2007

Related U.S. Application Data

(63) Continuation-in-part of application No. 10/165,099, filed on Jun. 6, 2002, now abandoned, which is a continuation-in-part of application No. 09/998,027, filed on Nov. 2, 2001, now abandoned, application No. 11/441,289, which is a continuation-in-part of application No. 11/046,346, filed on Jan. 28, 2005, now Pat. No. 7,459,287.

(60) Provisional application No. 60/684,136, filed on May 24, 2005, provisional application No. 60/245,756, filed on Nov. 3, 2000, provisional application No. 60/540,380, filed on Jan. 30, 2004.

(51) Int. Cl.
*G01N 33/574* (2006.01)

(52) U.S. Cl. .................................. 435/7.23; 435/7.1

(58) Field of Classification Search ........................ None
See application file for complete search history.

(56) References Cited

U.S. PATENT DOCUMENTS

| | | | |
|---|---|---|---|
| 3,854,480 | A | 12/1974 | Zaffaroni |
| 4,452,775 | A | 6/1984 | Kent |
| 5,239,660 | A | 8/1993 | Ooi |
| 7,459,287 | B2 | 12/2008 | D'Andrea |
| 2003/0093819 | A1 | 5/2003 | D'Andrea et al. |
| 2003/0188326 | A1 | 10/2003 | D'Andrea et al. |
| 2004/0002492 | A1 | 1/2004 | Murray Smith et al. |

FOREIGN PATENT DOCUMENTS

WO WO-0053169 A2 9/2000

OTHER PUBLICATIONS

Tockman et al (Cancer Res., 1992, 52:2711s-2718s).*
Zips et al. (2005, In Vivo, 19:1-7).*
Shimamura et al (Blood, Dec. 2002, 100:4649-4654).*
Ferrer et al (Clinical Lung Cancer, Jan. 2005, 6:250-254).*
Grover et al., "Cisplatin and the Sensitive Cell", Nature Medicine, vol. 9, No. 5, p. 513-514 (2003).
Andreassen et al., "ATR couples FANCD2 monoubiquitination to the DNA-damage response", *Genes Dev.*, 18:1958-1963 (2004).
Cheng et al., "Phase I clinical trial of curcumin, a chemopreventive agent, in patients with high-risk or pre-malignant lesions", *Anticancer Res.*, 21:2895-2900 (2001).
Chirnomas et al., "Chemosensitization to cisplatin by inhibitors of the Fanconi anemia/BRCA pathway", *Mol. Cancer Ther.*, 5(4):952-961 (2006).
D'Andrea et al., "The Fanconi Anaemia/BRCA Pathway", *Nat. Rev. Cancer*, 3:23-34 (2003).
Digweed et al., "Attenuation of the formation of DNA-repair foci containing RAD51 in Fanconi anaemia", *Carcinogenesis*, 23(7):1121-1126 (2002).
Dunn, F.B., "Heat shock protein inhibitor shows antitumor activity", *J. Natl. Cancer Inst.*, 94:1194-1195 (2002).
Egan et al., "Curcumin, a major constituent of turmeric, corrects cystic fibrosis defects", *Science*, 304:600-602 (2004).
Garcia-Higuera et al., "Interaction of the Fanconi Anemia proteins and BRCA1 in a common pathway", *Mol. Cell.*, 7:249-262 (2001).
Gregory et al., "Regulation of the Fanconi anemia pathway by monoubiquination", *Seminars in Cancer Biology*, 13:77-82 (2003).
Haining et al., "Rapid assessment of Fanconi pathway function: A new diagnostic approach to Fanconi Anemia", *Blood*, 96(11):977 (Abstract Only).
Holzel et al., "FANCD2 protein is expressed in proliferating cells of human tissues that are cancer-prone in Fanconi anaemia", *J. Pathology*, 201:198-203 (2003).
Inagaki et al., "N-(2-Aminoethyl)-5-isoquinolinesulfonamide, a newly synthesized protein kinase inhibitor, functions as a ligand in affinity chromatography. Purification of Ca2+-activated, phospholipid-dependent and other protein kinases", *J. Biol. Chem.*, 260(5):2922-2925 (1985).
Ito et al., "A potent inhibitor of protein kinase C inhibits natural killer activity", *Int. J. Immunopharmacol.*, 10(3):211-216 (1988).
Kau et al., "A chemical genetic screen identifies inhibitors of regulated nuclear export of a Forkhead transcription factor in PTEN-deficient tumor cells", *Cancer Cell.*, 4:463-476 (2003).
Lensch et al., "Acquired FANCA dysfunction and cytogenic instability in adult acute myelogenous leukemia", *Blood*, 102(1):7-16 (2003).
Nakanishi et al., "Interaction of FANCD2 and NBS1 in the DNA damage response", *Nat. Cell Biol.*, 4:913-920 (2002).
Sausville et al., "Inhibition of CDKs as a therapeutic modality", *Ann. N. Y. Acad. Sci.*, 910:207-221 (2000).
Schnur et al., "Inhibition of the oncogene product p185$^{erbB-2}$ in vitro and in vivo by geldanamycin and di hydrogeldanamycin derivatives", *J. Med. Chem.*, 38:3806-3812 (1995).
Schultz et al., "Paullones, a series of cyclin-dependent kinase inhibitors: synthesis, evaluation of CDK1/cyclin B inhibition, and *in vitro* antitumor activity", *J. Med. Chem.*, 42:2909-2919 (1999).

(Continued)

*Primary Examiner*—Laura B Goddard
(74) *Attorney, Agent, or Firm*—Mintz Levin Cohn Ferris Glovsky and Popeo, P.C.; Ivor R. Elrifi; Cynthia A. Kozakiewicz

(57) ABSTRACT

Disclosed herein are methods and compositions for the treatment of cancer. In particular, the present invention discloses inhibitors of the Fanconi anemia pathway and methods using same. Such inhibitors are useful in inhibiting DNA damage repair and can be useful, for example, in the treatment of cancer.

7 Claims, 24 Drawing Sheets

OTHER PUBLICATIONS

Taniguchi et al., "Convergence of the fanconi anemia and ataxia telangiectasia signaling pathways", *Cell*, 109:459-472 (2002).

Taniguchi et al., "Disruption of the Fanconi anemia-BRCA pathway in cisplatin-sensitive ovarian tumors", *Nat. Med.*, 9(5):568-574 (2003).

Taniguchi et al., "DNA damage-induced association of the Fanconi Anemia protein, FANCD2, with BRCA1 nuclear foci", *Blood*, 96(11):2402 (Abstract Only), 2000.

Taniguchi et al., "Molecular pathogenesis of Fanconi anemia: recent progress", *Blood*, 107(11):4223-4233 (2006).

Timmers et al., "Positional Cloning of a Novel Fanconi Anemia Gene, *FANCD2*", *Mol. Cell.*, 7:241-248 (2001).

Yang et al., "P-glycoprotein expression in ovarian cancer cell line following treatment with cisplatin", *Oncol. Res.*, 7(12):619-624 (1995).

* cited by examiner

1. Dispense PD20EGFP-D2 clone7 cells in 384-well plates
   4000 cells/well (133 cells/µl x 30µl)
2. Add chemical compound ( final conc. about 40µM)
3. Irradiate cells with 15Gy
4. Fix cells in 4% paraformaldehyde/ 0.125% Triton X-100/DAPI

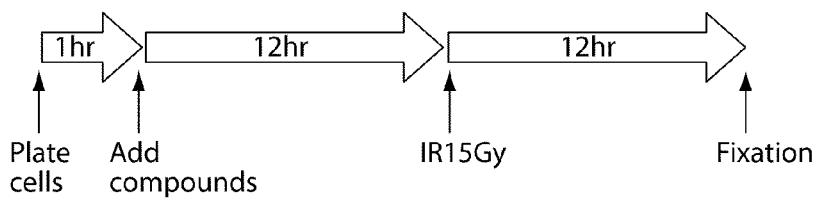

Plate cells | Add compounds | IR15Gy | Fixation

2. Take pictures with an automated microscope.
6. Score the effect of each compound.
7. Confirm the score with an inverted microscope by manual focusing.
8. Confirm the effect of the "effective" compound by FANCD2 western blotting, etc.

Fig. 6

COMPOSITIONS AND METHODS FOR THE TREATMENT OF CANCER

RELATED APPLICATIONS

This application claims the benefit of U.S. provisional application 60/684,136, filed May 24, 2005. This application is also a continuation-in-part of co-pending U.S. application Ser. No. 10/165,099, filed Jun. 6, 2002, which is a continuation-in-part of U.S. application Ser. No. 09/998,027, filed Nov. 2, 2001, now abandoned, which claims the benefit of U.S. provisional application 60/545,756, filed Nov. 3, 2000. This application is also a continuation-in-part of co-pending U.S. application Ser. No. 11/046,346, filed Jan. 28, 2005, which claims the benefit of U.S. provisional application 60/540,380, filed Jan. 30, 2004. Each of the aforementioned applications is hereby incorporated by reference in its entirety.

GOVERNMENT SUPPORT

This invention was made with government support under grants DK43889 and HL52725 from the National Institutes of Health. The U.S. Government has certain rights in the invention.

FIELD OF THE INVENTION

This invention generally relates to compositions and methods for the treatment of cancer.

BACKGROUND OF THE INVENTION

Many kinds of cancer resist effective chemotherapeutic treatment. In ovarian cancer, resistance is observed towards chemotherapeutic agents such as cisplatin. Cisplatin (cis-diamminedichloroplatinum, or CDDP), discovered originally in the late 1960s, is a cytotoxic drug used to treat many cancers, including ovarian cancer. Cisplatin acts by platination of DNA, resulting in DNA crosslinking. Up to 50% of ovarian carcinomas are intrinsically resistant to conventional chemotherapeutic agents such as cisplatin or other related platinum therapies. Many mechanisms of resistance have been postulated. However, the precise mechanism(s) underlying the intrinsic and extrinsic resistance to chemotherapy has not been elucidated. One method of reversing resistance to chemotherapy involves the use of chemosensitizers. Chemosensitizers generally inhibit the mechanism of resistance. Examples include verapamil, reserpine, tamoxifen and cremophor, inhibitors of efflux pumps conferring multidrug resistance (MDR1, P-glycoprotein). However, such chemosensitizers are effective only in a subset of tumors where drug efflux is the main mechanism of resistance. In addition, a number of these chemosensitizers have undesirable side effects.

SUMMARY OF THE INVENTION

In one aspect, the invention provides a method of predicting whether a subject with a neoplastic disorder or disease will respond to a genotoxic anti-neoplastic agent. The method comprises obtaining a biological sample from the subject, and determining degree of ubiquitination of the Fanconi anemia complementation group D2 (FANC D2) polypeptide within the biological sample. A degree of ubiquitination of the FANC D2 polypeptide in the biological sample of the subject that is less than about 70% when compared with a biological sample from a control subject is indicative of a subject that will respond to a genotoxic anti-neoplastic agent.

In another aspect, the invention provides a method of predicting whether a subject with a neoplastic disorder or disease will respond to a genotoxic anti-neoplastic agent. The method comprises obtaining a biological sample from the subject, and determining the FANC D2-containing foci within the biological sample. A difference in foci formation, wherein the sample from the subject that contains less than about 70% of the FANC D2-containing foci when compared with the biological sample from a control subject is indicative of a subject that will respond to a genotoxic anti-neoplastic agent.

In another aspect, a method of identifying an inhibitor of a non-FA DNA damage repair pathway is provided. The method comprises the following steps: (a) providing a control cell that is functional in the Fanconi Anemia (FA) pathway; (b) providing a test cell that is isogenic to the test cell but is defective in the FA pathway; (c) contacting the test cell and the control cell with a test compound; and, (d) comparing the sensitivity of the test cell and said control cell to the test compound. An increased sensitivity of the test cell to the test compound than the control cell is indicative of a test compound being an inhibitor of a non-FA DNA damage repair pathway.

In yet another aspect, a method of treating a neoplastic disorder in a subject in need thereof is provided. The method comprises administering to the subject a combination of an effective amount of: (a) an inhibitor of the FA pathway or pharmaceutically acceptable salts, esters, derivatives, solvates or prodrugs thereof, and (b) a genotoxic anti-neoplastic agent.

In still another aspect, a method of treating a neoplastic disorder in a subject in need thereof is provided. The method comprises administering to the subject a combination of an effective amount of: (a) an inhibitor of the FA pathway or pharmaceutically acceptable salts, esters, derivatives, solvates or prodrugs thereof, and (b) an inhibitor of a non-FA DNA damage repair pathway.

In another aspect, a method of treating a neoplastic disorder in a subject in need thereof is provided. The method comprises administering to the subject a combination of an effective amount of: (a) an inhibitor of the FA pathway or pharmaceutically acceptable salts, esters, derivatives, solvates or prodrugs thereof, (b) an inhibitor of a non-FA DNA damage repair pathway, and (c) a genotoxic anti-neoplastic agent or pharmaceutically acceptable salts, esters, derivatives, solvates or prodrugs thereof.

In another aspect, a method of increasing the sensitivity of a neoplastic disorder to a genotoxic anti-neoplastic agent is provided. The method comprises administering, before, after or concurrently with a therapeutically effective dose of the agent an effective amount of an inhibitor of the FA pathway.

In a final aspect, a method of increasing the sensitivity of a neoplastic disorder to a genotoxic anti-neoplastic agent is provided. The method comprises administering, before, after or concurrently with a therapeutically effective dose of the agent a combination of an effective amount of (a) an inhibitor of the FA pathway or pharmaceutically acceptable salts, esters, derivatives, solvates or prodrugs thereof, and (b) an inhibitor of a non-FA DNA damage repair pathway.

BRIEF DESCRIPTION OF THE FIGURES

FIG. 6 outlines a method for screening for FA inhibitors by fluorescence microscopy.

DETAILED DESCRIPTION OF THE INVENTION

Figure 1:
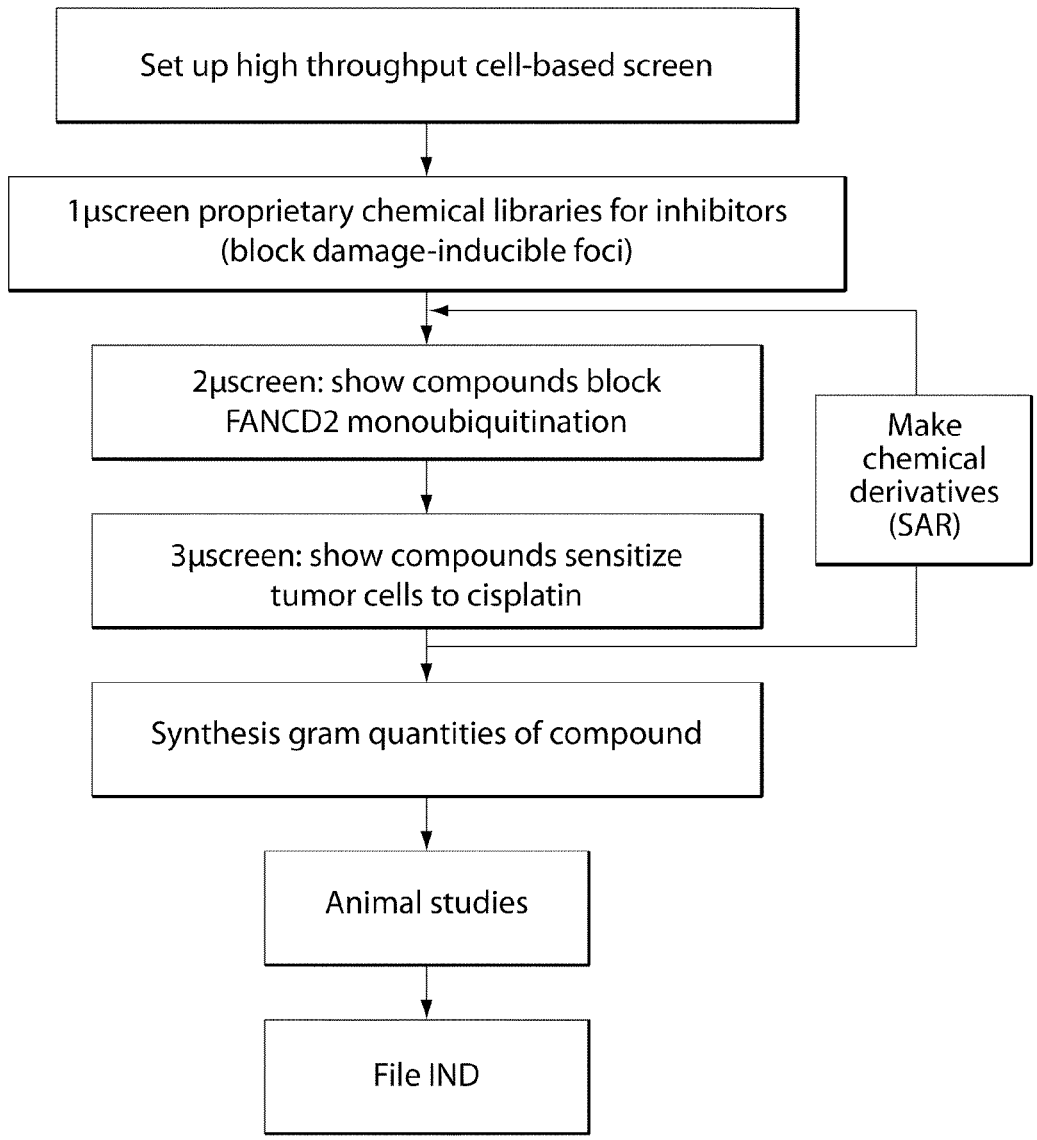
FIG. 1 outlines an example of the workflow of screens for the identification of inhibitors and agonists of the FA pathway.
Figure 2:
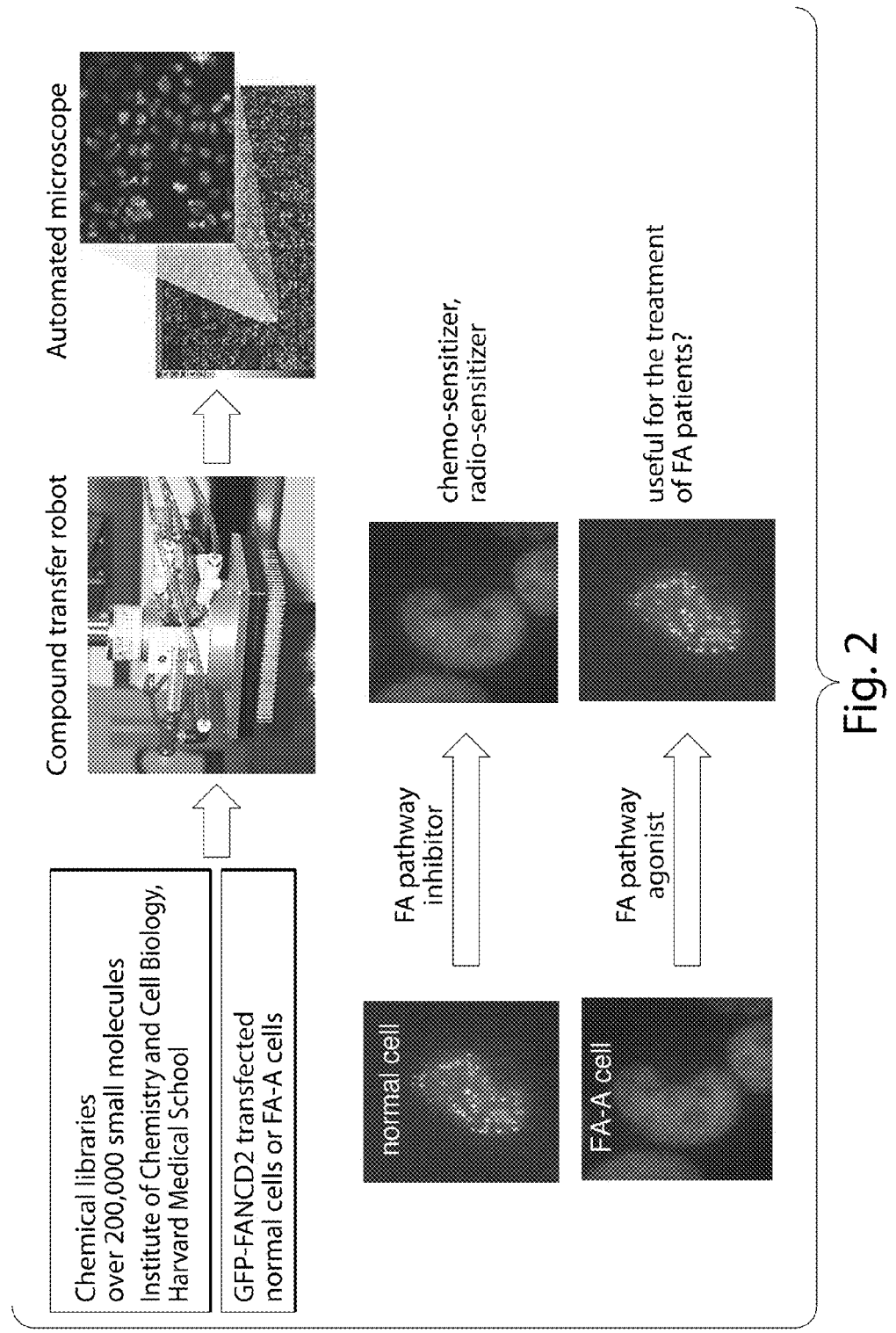
FIG. 2 outlines the high-throughput scheme for identification of FA pathway agonists and antagonists using fluorescence microscopy.
Figure 3:
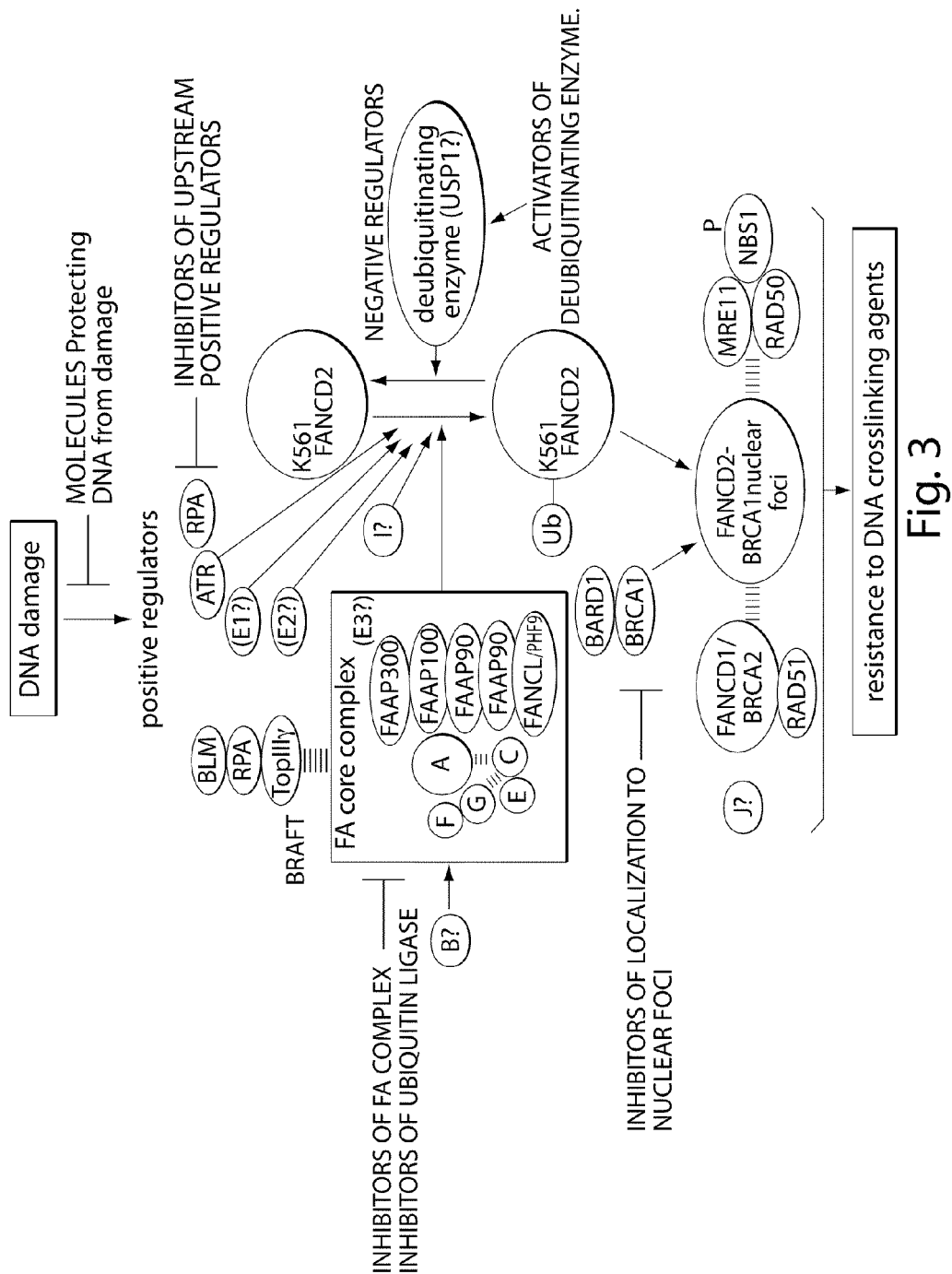
FIG. 3 is a schematic showing the protein components identified within the FA pathway of DNA damage repair
Figure 4:
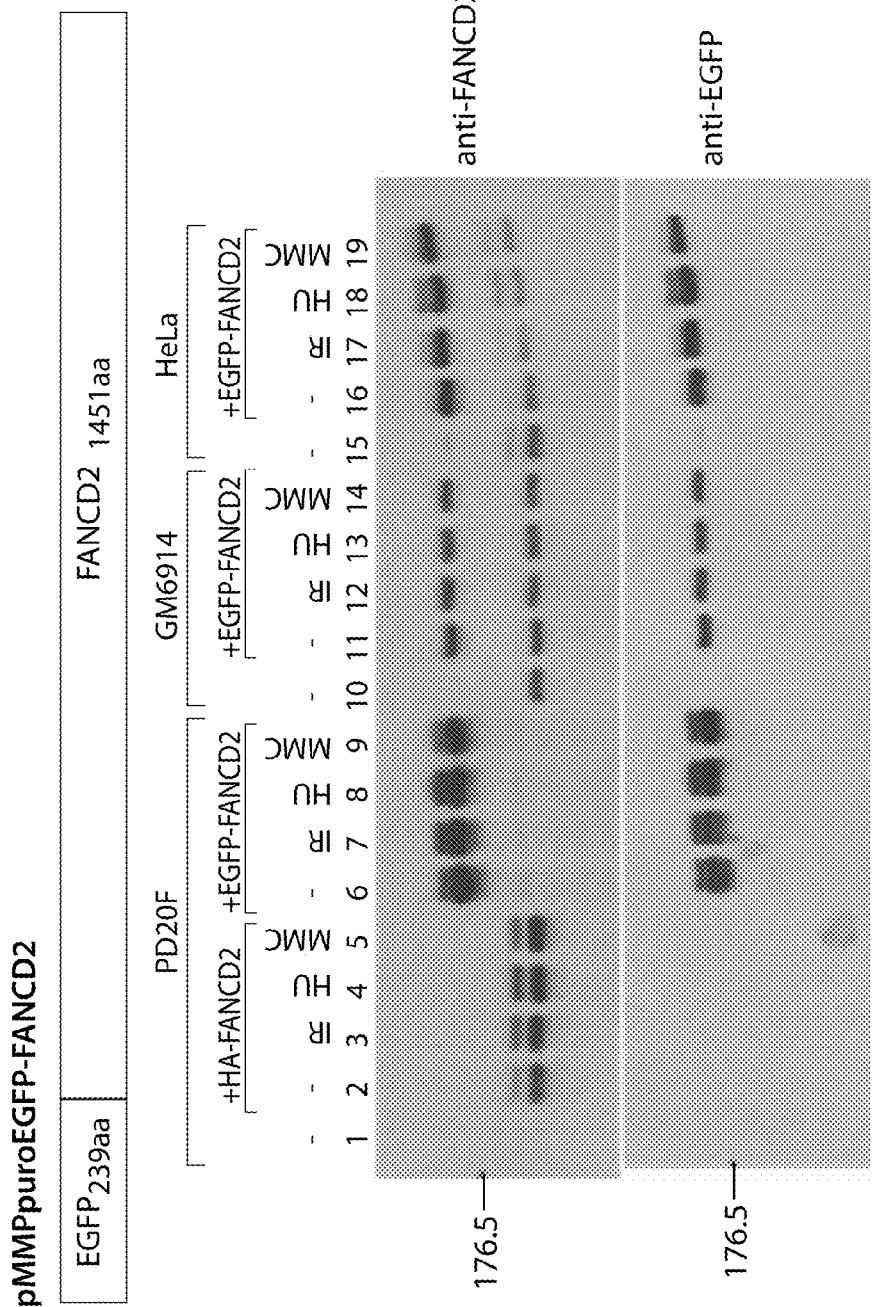
FIG. 4 shows the schematic of eGFP-FANC D2 fusion construct, and its ubiquitination in transfected PD20F, GM6914 and HeLa cells upon exposure to ionizing radiation (IR), HU, or Mitomycin C (MMC).
Figure 5:
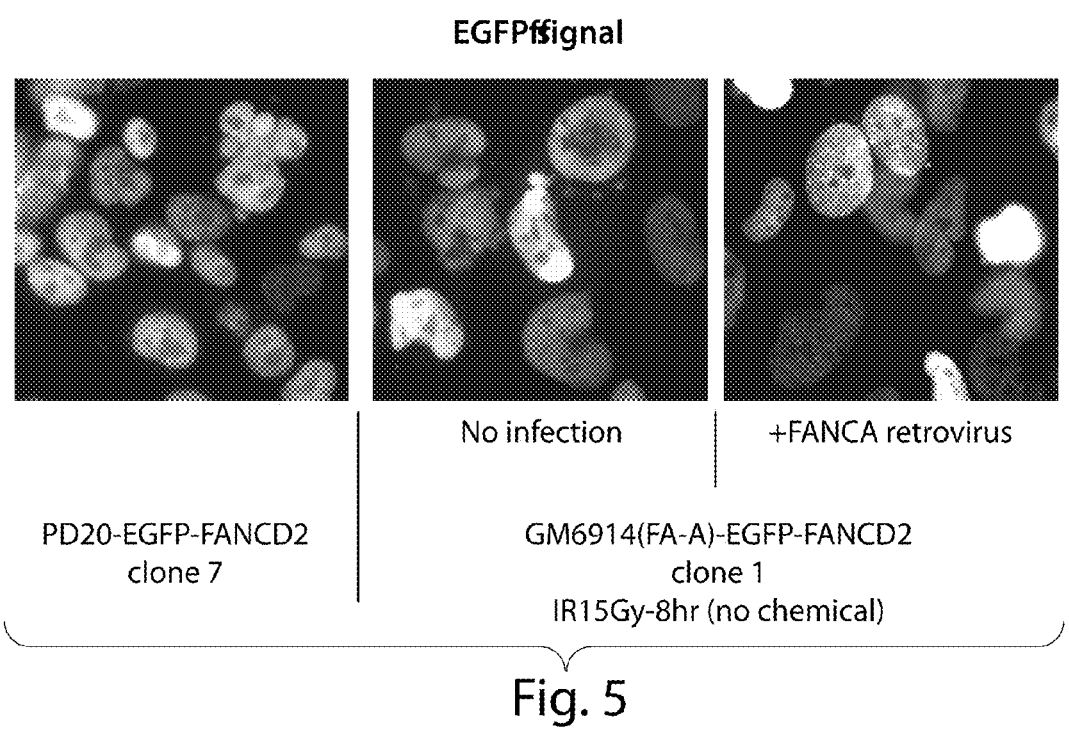
FIG. 5 are fluorescence micrographs showing the fluorescence signal emitted by eGFP-FANC D2 transfected PD20 and GM6914 cells. GM6914 cells additionally transfected with FANCA shows punctate, FANC D2-containing foci upon exposure to ionizing radiation.

The present invention is based in part on a series of discoveries showing the critical role played by the FA pathway in the sensitivity of cancers to anti-neoplastic agents. The role of the FA pathway in modulating the sensitivity of neoplastic disorders and/or cancer cells to anti-neoplastic agents has been demonstrated using cell lines deficient in FA pathway components, and using inhibitors of the FA pathway. Therefore; in one embodiment, a method for treating a subject with a neoplastic disorder is provided. One such method comprises administering an effective dose of an FA pathway inhibitor in combination with a genotoxic anti-neoplastic agent. Another method comprises administering an effective dose of an FA pathway inhibitor in combination with an inhibitor of a non-FA DNA damage repair pathway. Also provided are compositions useful for the treatment of neoplastic disorders comprising an FA pathway inhibitor in combination with a genotoxic anti-neoplastic agent and/or an inhibitor of a non-FA DNA damage repair pathway. Also provided are pharmaceutical compositions, as well as kits thereof, comprising FA pathway inhibitors and anti-neoplastic agents and/or an inhibitor of a non-FA DNA damage repair pathway.

Also provided are methods of identifying agents which modulate the FA pathway. Such methods are useful in identifying inhibitors of the FA pathway. Inhibitors thus identified are potentially useful as chemosensitizing and/or radiosensitizing agents. Also provided in the present invention are methods for identifying a non-FA DNA damage repair pathway inhibitor to be used in combination with the FA pathway inhibitor. The combination of the inhibitors may be useful to administer to patients receiving anti-neoplastic agents.

I. Definitions

As used herein, the terms "neoplasm", "neoplastic disorder", "neoplasia" "cancer," "tumor" and "proliferative disorder" refer to cells having the capacity for autonomous growth, i.e., an abnormal state or condition characterized by rapidly proliferating cell growth which generally forms a distinct mass that show partial or total lack of structural organization and functional coordination with normal tissue. The terms are meant to encompass hematopoietic neoplasms (e.g. lymphomas or leukemias) as well as solid neoplasms (e.g. sarcomas or carcinomas), including all types of pre-cancerous and cancerous growths, or oncogenic processes, metastatic tissues or malignantly transformed cells, tissues, or organs, irrespective of histopathologic type or stage of invasiveness. Hematopoietic neoplasms are malignant tumors affecting hematopoietic structures (structures pertaining to the formation of blood cells) and components of the immune system, including leukemias (related to leukocytes (white blood cells) and their precursors in the blood and bone marrow) arising from myeloid, lymphoid or erythroid lineages, and lymphomas (relates to lymphocytes). Solid neoplasms include sarcomas, which are malignant neoplasms that originate from connective tissues such as muscle, cartilage, blood vessels, fibrous tissue, fat or bone. Solid neoplasms also include carcinomas, which are malignant neoplasms arising from epithelial structures (including external epithelia (e.g., skin and linings of the gastrointestinal tract, lungs, and cervix), and internal epithelia that line various glands (e.g., breast, pancreas, thyroid). Examples of neoplasms that are particularly susceptible to treatment by the methods of the invention include leukemia, and hepatocellular cancers, sarcoma, vascular endothelial cancers, breast cancers, central nervous system cancers (e.g. astrocytoma, gliosarcoma, neuroblastoma, oligodendroglioma and glioblastoma), prostate cancers, lung and bronchus cancers, larynx cancers, esophagus cancers, colon cancers, colorectal cancers, gastro-intestinal cancers, melanomas, ovarian and endometrial cancer, renal and bladder cancer, liver cancer, endocrine cancer (e.g. thyroid), and pancreatic cancer.

A "genotoxic agent" or "genotoxin" refers to any chemical compound or treatment method that induces DNA damage when applied to a cell. Such agents can be chemical or radioactive. A genotoxic agent is one for which a primary biological activity of the chemical (or a metabolite) is alteration of the information encoded in the DNA. Genotoxic agents can vary in their mechanism of action, and can include: alkylating agents such as ethylmethane sulfonate (EMS), nitrosoguanine and vinyl chloride; bulky addition products such as benzo(a)pyrene and aflatoxin B1; reactive oxygen species such as superoxide, hydroxyl radical; base analogs such as 5-bromouracil; intercalating agents such as acridine orange and ethidium bromide.

A "genotoxic anti-neoplastic agent", as used herein, is a genotoxic agent used for chemotherapy, for example, to treat cancer. In particular, "genotoxic anti-neoplastic agents" encompass agents, both chemical or otherwise, which cause damage to DNA. These agents include DNA alkylating agents, intercalating agents, and the like. Non-limiting examples of "genotoxic anti-neoplastic agents" include 1,3-Bis(2-Chloroethyl)-1-NitrosoUrea (BCNU), Busulfan, Carboplatin, Carmustine, Chlorambucil, Cisplatin, Cyclophosphamide, Dacarbazine, Daunorubicin, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide, and Topotecan. "Genotoxic anti-neoplastic agents" also include radiation, in particular the types used in radiation therapy for the treatment of cancer, in a dosages sufficient to cause damage to DNA in a subject.

"DNA damage", as used herein, refers to chemical and/or physical modification of the DNA in a cell, including methylation, alkylation double-stranded breaks, cross-linking, thymidine dimers caused by ultraviolet light, and oxidative lesions formed by oxygen radical binding to DNA bases.

As used herein, a "chemosensitizer" and "chemosensitizing agent" refer to a compound which, when administered in a therapeutically effective amount in a subject, increases the sensitivity to chemotherapy compounds, and/or increases the therapeutic efficacy of the compounds, for example, in the treatment of a disease, such as neoplastic diseases, benign and malignant tumors, and cancerous cells. An increase in sensitivity to chemotherapy compounds, including genotoxic anti-neoplastic agents, can be measured, for example, by measuring the decrease in $LD_{50}$ of a cell towards a compound in the presence of the chemosensitizer.

Similarly, a "radiosensitizer" and "radiosensitizing agent", as used herein, refer to a compound which, when administered in a therapeutically effective amount in a subject, increases the sensitivity to radiation therapy (treatment by electromagnetic radiation), and/or increases the therapeutic efficacy of radiation therapy, for example, in the treatment of a disease, such as neoplastic diseases, benign and malignant tumors and cancer cells. Also contemplated are electromagnetic radiation treatment of other diseases not listed herein.

By "sample" or "biological sample" is meant any cell or tissue, or cell or tissue-containing composition or isolate derived from the subject. The sample may be derived from heart, brain, placenta, liver, skeletal muscle, kidney, pancreas, spleen, thymus, prostate, testis, uterus, small intestine, or colon. Another type of biological sample may be a preparation containing white blood cells, e.g., peripheral blood, sputum, saliva, urine, etc., for use in detecting the presence or absence of DNA damage in a subject that has been exposed to a genotoxic agent, such as radiation, chemicals, etc.

As used herein, "degree of ubiquitination" of the FANC D2 polypeptide refers generally to the level of activation of the FA pathway, as measured by the degree of monoubiquitination of the FANC D2 polypeptide within a subject or biological sample therefrom. As used herein, the "degree of ubiquitination" of the FANC D2 polypeptide can encompass the proportion of total FANC D2 polypeptide within a sample that is monoubiquitinated, and can be expressed on a fractional or percentage basis. As used herein, the "degree of ubiquitination" of the FANC D2 polypeptide can also be measured using any substitute methods of detecting activation of the FA pathway, including the degree of foci formation.

As used herein, "degree of foci formation" refers to the total number or the rate of formation of FANC D2-containing foci in a sample. FANC D2-containing foci are nuclear protein complexes formed in response to the activation of the FA pathway, for example by exposure to a genotoxic agent. FANC D2-containing foci can be detected, for example, by immunofluorescence microscopy using a labeled antibody directed against the FANC D2 polypeptide, as further described herein. In certain cases, FANC D2-containing foci can also be detected in cells expressing a functional fusion protein comprising GFP and the FANC D2 polypeptide. In these cells, FANC D2-containing foci can be detected using fluorescence microscopy without the use of anti-FANC D2 antibodies. The degree of foci formation can be normalized from one sample to another, for example, to total number of cells, total number of intact nuclei, total sample volume, or total sample mass.

By "difference in foci formation" is meant a difference, whether higher or lower, in the number, size or persistence of FANC D2-containing foci, when comparing a test sample with either a control sample or reference sample. A difference includes an increase or decrease that is 2-fold or more, or less, for example 5, 10, 20, 100, 1000-fold or more as compared to a control or reference sample. A difference also includes an increase or decrease that is 5% more or less, for example, 10%, 20%, 30%, 50%, 75%, 100%, as compared to a control or reference sample.

"Modulate" formation of FANC D2-containing foci, as used herein, refers to a change or an alteration in the formation of FANC D2-containing foci in a biological sample. Modulation may be an increase or a decrease in foci number, size or persistence within a biological sample, and includes an increase or decrease that is 2-fold or more, or less, for example 5, 10, 20, 100, 1000-fold or more as compared to a control or reference sample. Modulation may also be an increase or decrease that is 5% more or less, for example, 10%, 20%, 30%, 50%, 75%, 100%, as compared to a control or reference sample.

As used herein, exposure to a "low level" of a genotoxic anti-neoplastic agent refers to exposure to a dose of a particular genotoxic anti-neoplastic agent which results in no more than 20% of the maximal number of FANC D2-containing foci in biological samples. Because of the multitude of genotoxic anti-neoplastic agents to which a sample may be exposed, as well as the varying sensitivities of different samples to such genotoxic anti-neoplastic agents, it is preferable to express the dosage relative to the formation of FANC D2-containing foci, rather than in the absolute dose of a particular genotoxic anti-neoplastic agent.

The term "modulator" refers to a chemical compound (naturally occurring or non-naturally occurring), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. Modulators are evaluated for potential activity as inhibitors or activators (directly or indirectly) of a biological process or processes (e.g., agonist, partial antagonist, partial agonist, antagonist, anti-neoplastic agents, cytotoxic agents, inhibitors of neoplastic transformation or cell proliferation, cell proliferation-promoting agents, and the like) by inclusion in screening assays described herein. The activities (or activity) of a modulator may be known, unknown or partially-known. Such modulators can be screened using the methods described herein.

The term "candidate modulator" refers to a compound to be tested by one or more screening method(s) of the invention as a putative modulator. Usually, various predetermined concentrations are used for screening such as 0.01 µM, 0.1 µM, 1.0 µM, and 10.0 µM, as described more fully below. Test compound controls can include the measurement of a signal in the absence of the test compound or comparison to a compound known to modulate the target.

As used herein, an "FA pathway inhibitor" and "inhibitor of the FA pathway" refer to a chemical compound (naturally occurring or non-naturally occurring), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. An "FA pathway inhibitor" and "inhibitor of the FA pathway" refer broadly to compounds which inhibit the ability of the FA pathway to repair DNA damage. Inhibition of the FA pathway by an "FA pathway inhibitor" or an "inhibitor of the FA pathway" can be assessed using the techniques described herein, including without limitation, the detection of FANC D2-containing foci and detection of monoubiquitination of the FANC D2 polypeptides. As will be appreciated by one skilled in the art, the method contemplates any other method currently known or known in the future, for the detection of the inhibition of the FA pathway. Inhibition may be a decrease in number, size or persistence of FANC D2-containing foci, and includes a decrease that is 2-fold or more, for example, 2, 5, 10, 20, 100, 1000-fold or more as compared to a control or reference. Inhibition may also be an decrease of 5% or more, for example 5%, 10%, 20%, 30%, 50%, 75%, or up to 100%, as compared to a control or reference. In addition, as used herein, an "FA pathway inhibitor" and "inhibitor of the FA pathway" encompass the pharmaceutically acceptable salts, solvates, esters, derivatives or prodrugs.

A "non-FA DNA damage repair pathway", as used herein, refers to any of the DNA damage repair pathways selected from the group consisting of the direct reversal, non-homologous end joining (NHEJ), base excision repair (BER), nucleotide excision repair (NER), and mismatch repair (MR) pathways.

The pharmaceutical compositions of the present invention can be administered using any amount and any route of administration effective for increasing the therapeutic efficacy of drugs. As used herein, "therapeutically effective amount," when used in combination with a chemosensitizer or radiosensitizer, refers to a sufficient amount of the chemosensitizing agent to provide the desired effect against target cells or tissues. The exact amount required will vary from subject to subject, depending on the species, age, and general condition of the subject; the particular chemosensitizing agent; its mode of administration; and the like.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "therapeutically effective dose" refers to that amount of protein or its antibodies, antagonists, or inhibitors which prevent or ameliorate the symptoms or conditions, for example, a neoplastic disorder. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Pharmaceutical compositions which exhibit large therapeutic indices are preferred. The data obtained from cell culture assays and animals studies is used in formulating a range of dosage for human use. The dosage of such compounds lies preferably within a range of circulating concentrations that include the ED50 with little or no toxicity. The dosage varies within this range depending upon the dosage from employed, sensitivity of the patient, and the route of administration.

The exact dosage is chosen by the individual physician or veterinarian in view of the patient to be treated. Dosage and administration are adjusted to provide sufficient levels of the active moiety or to maintain the desired effect. Additional factors which may be taken into account include the severity of the disease state; age, weight and gender of the subject; diet, time and frequency of administration, drug combination(s), reaction sensitivities, and tolerance/response to therapy. Long acting pharmaceutical compositions might be administered every 3 to 4 days, every week, or once every two weeks depending on a half-life and clearance rate of the particular formulation.

The term "pharmaceutically acceptable salt" refers to both acid addition salts and base addition salts. The nature of the salt is not critical, provided that it is pharmaceutically acceptable. Exemplary acid addition salts include, without limitation, hydrochloric, hydrobromic, hydroiodic, nitric, carbonic, sulfuric, phosphoric, formic, acetic, citric, tartaric, succinic, oxalic, malic, glutamic, propionic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric, galacturonic acid and the like. Suitable pharmaceutically acceptable base addition salts include, without limitation, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine, procaine and the like. Additional examples of pharmaceutically acceptable salts are listed in *Journal of Pharmaceutical Sciences* (1977) 66:2. All of these salts may be prepared by conventional means from a modulator of FANC D2-containing foci by treating the compound with the appropriate acid or base.

II. FANC D2 Foci

The cellular response to DNA damage is a complex interacting network of pathways that mediate cell cycle checkpoints, DNA repair, and apoptosis. A model lesion for the investigation of these pathways has been DNA double-strand breaks, which rapidly induce cell cycle checkpoints and are repaired by a number of different pathways. In mammalian cells, both homologous recombination and nonhomologous recombination pathways are utilized. Extensive studies in mammalian cells have shown that complexes of DNA repair and cell cycle checkpoint proteins rapidly localize to sites of double-strand breaks induced by ionizing radiation. These proteins create foci that can be detected by immunofluorescent analyses.

The Fanconi anemia complementation group D2 (FANC D2) is a component of a protein complex involved in chromosome stability and repair. Fanconi anemia (FA) is a hereditary disorder characterized, in part, by a deficient DNA-repair mechanism that increases a person's risk for a variety of cancers. In response to DNA damage, the FA complex activates FANC D2, which then associates with Breast Cancer, Type 1 polypeptide (BRCA1). Activation of FANC D2 occurs by phosphorylation of a serine 222 residue by the Ataxia-Telangiectasia Mutated (ATM) kinase. In addition, activation via the FA pathway occurs via monoubiquitination of FANC D2 at lysine 561. In its unmodified form, FANC D2 is diffusely located throughout the nucleus. When ubiquitinated, FANC D2 forms dots, or foci, in the nucleus. The ubiquitination of FANC D2 and subsequent formation of nuclear foci occurs in response to DNA damage. By coimmunoprecipitation, Nakanishi et al. found constitutive interaction between FANC D2 and Nijmegen Breakage Syndrome 1 (NBS1), providing evidence that these proteins interact in two distinct assemblies to mediate S-phase checkpoint and resistance to mitomycin C-induced chromosome damage (Nakashini et al., (2002) *Nat Cell Biol.* 4:913-20).

At least two types of ionizing radiation-induced foci have been observed: one containing the Rad5 1, BRCA1 and BRCA2 proteins, and another containing the Mre11-Rad50-NBS1 complex. Rad51 foci, which contain the tumor suppressor proteins BRCA1 and BRCA2, also appear during S phase in the absence of exogenous induction of DNA damage.

Mre11-Rad50-NBS1 foci can be detected as early as 10 min after irradiation and are clearly present at sites of DNA breaks, while DNA repair is ongoing. These foci also colocalize with the BRCA1 protein, which has been shown to be required for their formation, possibly through its physical interaction with human Rad50 (hRad50). In addition, coimmunoprecipitation experiments performed with BRCA1 have indicated the presence of a large number of additional proteins in this complex (referred to as the BRCA1-associated surveillance complex). These include the mismatch repair proteins Msh2, Msh6, and Mlh1, the checkpoint kinase ATM, the product of the Bloom's syndrome gene BLM, and replication factor C. BRCA1, NBS1, and hMre11 have all been shown to be substrates of the ATM kinase and to become phosphorylated in response to the presence of DNA breaks.

The present invention is related to the discovery that cells exposed to genotoxic anti-neoplastic agents form FANC D2-containing foci. Multiple DNA damage response proteins have now been identified which form nuclear foci, also called IRIFs (Ionizing-Radiation Inducible foci) in response to DNA damage. Methods of detecting FANC D2-containing foci, as well as detecting and quantitating the relative amount of ubiquitinated FANC D2 polypeptide are described in U.S. application Ser. No. 10/165,099 and U.S. App. No. 60/540, 380, the contents of which are incorporated in their entirety herein by reference.

III. Means of Detecting FANC D2 Activation

1. Detection Using FANC D2-binding 7 Ligands

The total cellular level of FANC D2 protein does not significantly change in response to DNA damage. Rather, DNA damage results in monoubiquitination of FANC D2, as well as recruitment into FANC D2-containing foci. It will be appreciated by one skilled in the art that an alternative to measuring the presence of FANC D2-containing foci is to use a ligand which specifically binds the monoubiquitinated, but not the unubiquitinated form of FANC D2. To detect the presence of monoubiquitinated FANC D2, the ligand is preferably associated with a detectable label as described above. The main advantage of using such a ligand, as will be appreciated by one skilled in the art, is that, due to the typically low basal level of monoubiquitinated FANC D2 in cells with undamaged DNA, the level of FANC D2-containing foci can be measured in a sample taken from a living subject using the level of monoubiquitinated FANC D2 as a surrogate marker. An antibody which specifically recognizes the monoubiquitinated form of FANC D2 (FANC D2-L) has considerable utility as a rapid diagnostic. For instance, this antibody could be used for:

1) Immunohistochemistry (IH). This antibody could be used to examine tissue sections prepared from solid tumors (e.g., breast, ovarian, lung tumors). A positive signal by IH would predict that the tumor will be resistant to cisplatin and related drugs.
2) FACS analysis. Peripheral blood lymphocytes (PBLs) could be screened with this antibody. A positive signal suggests the presence of activated FANC D2, consistent with a recent exposure of an individual to IR. or toxin. Thus, this antibody is a useful extension of the radiation dosimeter assay described in this application.
3) A high-throughput assay to screen for inhibitors of the purified FA complex. These inhibitors will block the ability of the FA complex to monoubiquitinate FANC D2 in vitro. The new monoclonal antibody will be a useful reagent for end product detection. Additional methods of measuring FANC D2-containing foci using a ligand which specifically recognizes monoubiquitinated FANC D2 include immunoblot analysis, or Enzyme linked immunosorbant assays (ELISA) using extracts of samples collected from living subjects, or FACS analysis (Harlow et al, 1999, *Using Antibodies: A Laboratory Manual*, Cold Spring Harbor Laboratory Press, NY).

A sensitive measure of IR exposure is the increased monoubiquitination of FANC D2. In undamaged cells, the ratio of FANC D2-L (monoubiquitinated isoform) to FANC D2-S (unubiquitinated isoform) is approximately 0.5-0.6. This ratio (L/S) is readily calculated by comparing the density of the L band to the S band on a western blot. A sensitive indicator of increased FANC D2 monoubiquitination and IR exposure is the conversion of the L/S ratio to 1.0 or greater.

2. Detection Using GFP-FANC D2 Fusion Proteins

An alternative approach for the detection of FANC D2 activation and foci formation is the use of a FANC D2 protein fused with a fluorescent protein, for example, GFP. A functional fusion protein of FANC D2 and GFP is able to form foci upon exposure to genotoxic anti-neoplastic agents. These foci are then visible by fluorescence microscopy. Therefore, formation of FANC D2-containing foci can be measured as a surrogate marker for activation of the FA pathway in response to exposure to genotoxic anti-neoplastic agents. Methods of generating such fusion protein constructs, as well as methods for detecting formation of FANC D2-containing foci are described in U.S. App. No. 60/540,380, which is incorporated herein by reference.

IV. Identifying Inhibitors of the FA Pathway

The present invention encompasses methods and compositions useful for the treatment of neoplastic diseases using inhibitors of the FA pathway. Inhibitors of the FA pathway can be identified by methods described herein, and also methods previously described, for example, in U.S. application Ser. No. 10/165,099 and U.S. App. No. 60/540,380, the contents of which are incorporated herein by reference. For example, inhibitors of the FA pathway can be identified systematically using a three-tiered approach, as summarized in FIG. 1.

The first tier of screening comprises a high-throughput method to identify agents which alter the formation of FANC D2-containing foci. Detection of FANC D2-containing foci, for example by using a FANC D2 ligand such as anti-FANC D2 antibodies or cell lines expressing a functional eGFP-FANC D2 fusion protein, are described in U.S. application Ser. No. 10/165,099 and U.S. App. No.60/540,380, the contents of which are incorporated herein by reference. The method comprises contacting cells or a biological sample with a test compound simultaneously with, before or after exposure to a genotoxic anti-neoplastic agent, for example ionizing radiation (IR), mitomycin C or cisplatin, at a dosage which induces formation of FANC D2-containing foci. The number and size FANC D2-containing foci are then detected in cells and compared with control cells which were not contacted with the test compound. A decrease in the number and/or size of FANC D2-containing foci relative to control cells is indicative of an agent which is an inhibitor of the FA pathway, whereas an increase in the number and/or size of FANC D2-containing foci relative to control cells is indicative of an agent which is an agonist of the FA pathway. Potential agonists and inhibitors thus identified can be further tested to determine whether they exert their effects directly on the FA pathway, or act indirectly, for example, by directly causing damage to DNA (in the case of potential agonists of the FA pathway), or by reducing the effect of the genotoxic anti-neoplastic agent that was used in the screen.

The second tier of screening involves the detection of ubiquitinated FANC D2 polypeptides. As previously described, activation of the FA pathway results in monoubiquitination of the FANC D2 polypeptide. Activation of the FA pathway can therefore be measured by detecting the relative amount of ubiquitinated FANC D2 compared with unubiquitinated FANC D2 polypeptide. The ubiquitination of FANC D2 can be detected by performing immunoblot analysis of protein extracts. Ubiquitinated FANC D2 migrates at a higher molecular weight band on immunoblot analyses, and can be detected using a labeled FANC D2 ligand, for example an anti-FANC D2 antibody. Therefore, the second tier of the screening comprises The method comprises contacting cells or a biological sample with a test compound simultaneously with, before or after exposure to a genotoxic anti-neoplastic agent, for example ionizing radiation (IR), mitomycin C or cisplatin, at a dosage which induces formation of FANC D2-containing foci. The amount of ubiquitinated FANC D2 polypeptide relative to unubiquitinated FANC D2 polypeptide is detected, and compared with samples from control cells or biological samples which were not contacted with the test compound. A difference in the relative amount of ubiquitinated FANC D2 relative to control cells indicates that the test compound is a modulator of the FA pathway. An increase in the relative amount of ubiquitinated FANC D2 polypeptide compared with control cells or biological samples is indicative of an agonist of the FA pathway, whereas a decrease in the relative amount of ubiquitinated FANC D2 polypeptide compared with control cells or biological samples is indicative of an inhibitor of the FA pathway. As described previously, the potential agonists and inhibitors thus identified can be further tested to determine whether they exert their effects directly on the FA pathway, or act indirectly, for example, by directly causing damage to DNA (in the case of potential agonists of the FA pathway), or by reducing the effect of the genotoxic anti-neoplastic agent that was used in the screen.

Figure 8:
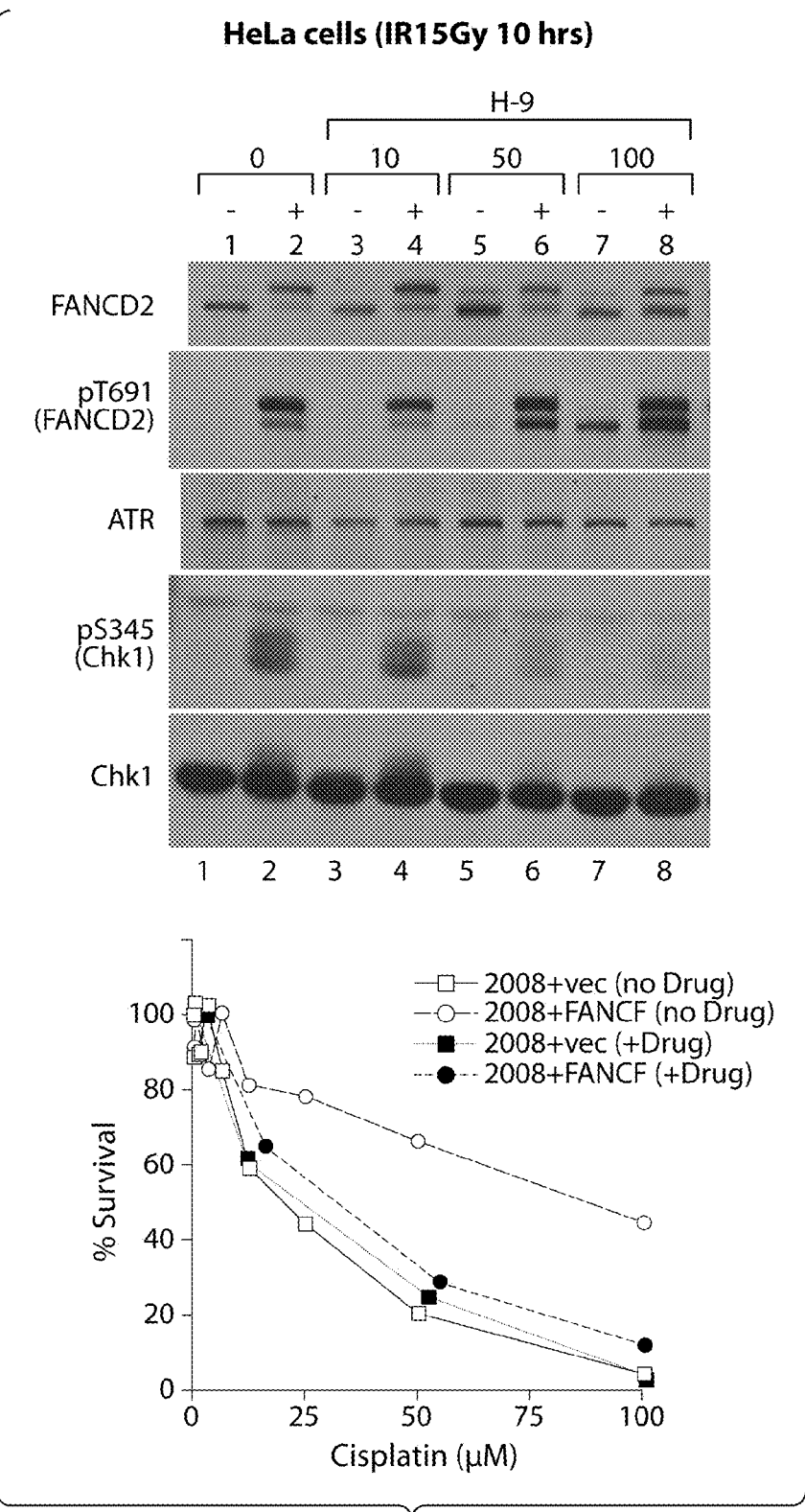
FIG. 8 shows an immunoblot analysis showing the effect of H-9 on inhibition of IR-inducible monoubiquitination of FANC D2 (top two panels), phosphorylation of ATR kinase (middle panel), Chk1 phosphorylation (fourth panel), and Chk1 polypeptide levels (bottom panel). The graph shows the enhanced sensitivity of 2008 cells to cisplatin by H-9. The 2008 cells are inherently sensitive to cisplatin because of a deficiency FANCF (Open Square). This sensitivity to cisplatin is reduced upon transfection of FANCF (2008+F, open circle). Treatment of 2008+F cells with H-9 re-establishes sensitivity to cisplatin (closed circle), while not affecting sensitivity to cisplatin in untransfected cells (closed square).

The third tier of screening comprises in vitro testing of compounds for sensitivity to genotoxic anti-neoplastic agents. Contacting cells or biological samples with inhibitors of the FA pathway would be expected to increase the sensitivity of the samples/cells to genotoxic anti-neoplastic agents. Specific inhibition of the FA pathway by a test agent is expected to increase the sensitivity to a degree comparable to, for example, a cell line with a specific defect in one or more components of the FA pathway. Cell lines useful for this type of assay include the ovarian cancer cell line, 2008, which is deficient in FANCF. 2008 cells deficient in FANCF show heightened sensitivity to genotoxic anti-neoplastic agents (see graph in FIG. 8, open rectangle), and this sensitivity is restored to wild-type levels by overexpression of the FANCF (FIG. 8, open circle). The role of FANCF in restoring wild-type levels of genotoxin sensitivity is then abolished by contacting with a test agent which inhibits the FA pathway (FIG. 8, closed circle), while leaving the sensitivity to the genotoxic anti-neoplastic agent unaffected in the absence of the FANCF transfection (FIG. 8, closed rectangle).

The three tiers of screening described above provide a stream-lined approach to rapidly identifying and characterizing potential modulators of the FA pathway. It should be understood that methods to identify modulators are not limited to the particular embodiments of the invention described above, and variations of the embodiments can be made and still fall within the scope of the invention. In addition, the terms used herein are for the purpose of describing the particular embodiments and are not intended to be limiting.

V. Inhibitors of the FA Pathway

The present invention contemplates the use of inhibitors of the FA pathway. An inhibitor of the FA pathway includes any compound which results in the inhibition of formation of FANC D2-containing foci, when administered before, after or concomitantly with a genotoxic anti-neoplastic agent(s) which normally cause formation of FANC D2-containing foci. Examples of genotoxic anti-neoplastic agents which induce formation of FANC D2-containing foci include, but are not limited to, ionizing radiation (IR) and DNA alkylating agents such as cisplatin or mitomycin C. Inhibition of the FA pathway can also be detected by measuring the relative amounts of ubiquitinated and unubiquitinated FANC D2 polypeptide of samples subjected to an agent which normally induces ubiquitination. Detection of FANC D2-containing foci using, for example, microscopic detection means, as well as determination of the relative ubiquitination state of the FANC D2 polypeptide, is described in U.S. Ser. No. 10/165099, filed Jun. 6, 2002, and U.S. Ser. No. 60/540380, filed Jan. 30, 2004, the contents of which are incorporated herein by reference. Briefly, FANC D2-containing foci can be detected using immunofluorescence microscopy, using anti-FANC D2 antibodies. Alternatively, a fluorescent protein-tagged version of FANC D2 can be transfected into the cells of interest, and formation of FANC D2-containing foci measured microscopically be detecting fluorescent 'foci', again, as described in U.S. Ser. No. 60/540,380. Compounds which inhibit the FA pathway, such as wortmannin and Trichostatin A, have previously been disclosed, for example in U.S. Ser. No. 60/540380, filed Jan. 30, 2004.

The present invention describes additional examples of inhibitors of the FA pathway, including curcumin, H-9 and alsterpaullone, which were identified using the screening methods described herein.

H-9

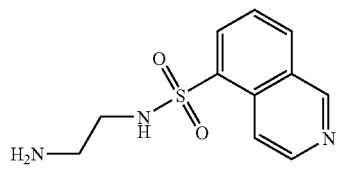

Formula I

Molecular weight 251.31

CAS Number 84468-17-7

H-9 kinase inhibitor, also known as N-2-Aminoethyl-5-Isoquinolinesulfonamide (formula I) is a known inhibitor of several kinases, including PKA, PKG, PKC, Calcium/Calmodulin dependent protein kinase, and myosin light chain kinase (Inagaki et al., (1985) *J Biol. Chem.* 260(5):2922-5; Ito et al., (1988) *Int. J Immunopharmacol.* 10:211-216)

Alsterpaullone

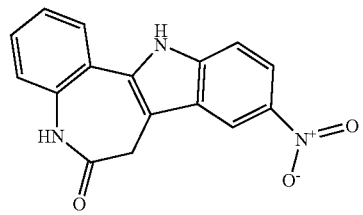

Formula II

Molecular weight 293.27696

Molecular formula C16H11N3O3

Alsterpaullone (formula II), is known to inhibit Cdk1/cycline B, Gsk-3B, and Cdk5 (Sausville et al. (2000) *Ann N Y Acad. Sci.* 910:207-221; Schultz et al. (1999) *J Med. Chem.* 42:2909-2919).

Curcumin

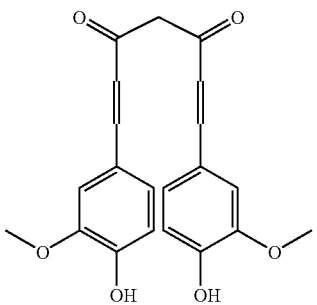

Formula III

CAS No.: 458-37-7

Molecular Weight: 368.39

Curcumin (Turmeric yellow, also known as 1,7-bis (4'-hydroxy-3'-methoxyphenyl)-1,6-heptadiene-3,5-dione, diferuloylmethane), a low molecular weight polyphenol derived from the spice, turmeric, is associated with regression of some solid tumors in humans (Cheng et al. (2001) *Anticancer Res.* 21:2895-2900). Curcumin is safe in human trials at doses as high as 8000 mg/day (Cheng et al, ibid.). Recent studies suggest that curcumin may have activity in the treatment of other human diseases, such as cystic fibrosis (Egan et al. (2004) *Science* 304:600-602).

Geldanamycin

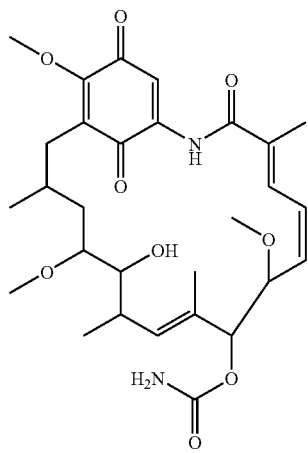

Formula IV

CAS number: 30562-34-6
Molecular Weight: 560.6

Geldanamycin (formula IV) is a benzoquinone ansamycin antibiotic which binds to Hsp90 (Heat Shock Protein 90) and alters its function. The present invention encompasses compositions and methods comprising geldanamycin and its analogs. Analogs of geldanamycin include 17-(Allylamino)-17-demethoxy-geldanamycin (Schnur et al., (1995) *J Med. Chem.* 38:3806-12; Dunn (2002) *J Natl. Cancer Inst* 94, 1194-5). The present invention further contemplates compositions and methods comprising other inhibitors of HSP90, in particular benzoquinone ansamycin inhibitors of HSP90, coumarin derivatives (described, for example, in WO 00/53169).

Other compounds which can inhibit the FA pathway include those compounds listed within Table 2. Therefore, the inhibitor of the FA pathway can be selected from the group consisting of Alsterpaullone, (±)13-HODE, nifedipine, penitrem A, Geladanamycin, Go6976, leukotriene B3, Trichostatin-A, AG-370, Mitomycin C, Amanitin (alpha-amanitin), HNMPA-(AM)3, Propidium iodide, DRB, Ochratoxin, Ca-074-Me, K252c, Wortmannin, Actinomycin D, AG213, BAPTA-AM, Curcumin, Puromycin, Bumetanide, Methyladenine [3-methyladenine], H9, TPEN, spermine NONOate, PD00600, 5323069, and 1M556S.

VI. Inhibitors of Other DNA Damage Repair Pathways

Cells are continuously subjected to different kinds of DNA damage. These damages can arise from exposure to a variety of internal and external chemicals and radiation, including reactive oxygen species such as superoxide ($O_2^-$), hydrogen peroxide ($H_2O_2$). In addition, humans are constantly exposed a vast array of carcinogens, many of which act by causing damage to the DNA. It has been shown that at least six distinct mechanisms exist for DNA damage repair in humans, depending upon the type of damage incurred.

Many cancers have a defect in at least one of the six major DNA damage repair pathways. In addition to causing increased genomic instability, disruption of any of these DNA repair mechanisms can lead to increased sensitivity to genotoxic anti-neoplastic agents. Therefore, these cancers have increased dependence on one of the other five DNA damage repair pathways for survival. Hence, disruption of a second, non-FA DNA damage repair pathway in these neoplastic disorders, for example by a small molecule inhibitor may result in selective cancer cell death. Stated differently, many cancers may turn out to have a dominant (primary) DNA damage repair pathway. Since one DNA damage repair pathway is already abolished or significantly reduced in the cancer, an extra burden is placed on the dominant pathway in order to maintain the high proliferation rate and to prevent DNA damage of these cells. Disruption of the dominant pathway in a cancer cell in which a major DNA damage repair pathway is abolished or diminished, by means of an exogenous inhibitor, may therefore have a profound cytotoxic effect on the tumor cells but a relatively small cytotoxic effect on the surrounding normal cells.

Loss of the FA/BRCA pathway leads to chromosome instability, increased cisplatin sensitivity, thus resulting in increased activity of the remaining non-FA DNA damage repair pathways, including the Base Excision Repair (BER) pathway. Accordingly, an inhibitor of a non-FA DNA damage repair pathway, for example, BER (such as a PARP1 inhibitor or an inhibitor of a specific kinase in the BER pathway) would be lethal to those cells, but may have little effect on normal (non-tumor) cells.

The present invention also contemplates the use of inhibitors of various other DNA damage repair pathways. As previously described, there are several major pathways for DNA damage repair, including but not limited to, non-homologous end joining (NHEJ), base excision repair (BER), nucleotide excision repair (NER), and mismatch repair (MR). These mechanisms are described, for example, in Hoeijmakers J H J (2001) Nature 411: 366-374, Svejstrup J Q (2002) Nat Rev Mol Cell Biol. 3: 21-29, and in Panasci, *DNA Repair in Cancer Therapy* Humana Press, 2004, Totowa, N.J., which are incorporated herein by reference.

A. Non-Homologous End Joining (NHEJ)

DNA double strand breaks (DSBs) can be caused by any number of environmental or other factors, including reactive oxygen species, ionizing radiation (IR) and certain anti-neoplastic drugs like bleomycin. Failure to repair DSBs can lead to a number of consequences, including mutations, chromosomal aberrations, and eventually cell death. Non-homologous end-joining (NHEJ), also called illegitimate recombination, is one major pathway of repairing DSBs. Some members of the NHEJ pathway are shown in Table 1.

TABLE 1

Genes and Proteins Important for NEHJ

| Gene name | Protein name; function |
|---|---|
| MRE11 | Exonuclease (3' to 5') |
| NBS1 | Mre11-interaction |
| RAD50 | Role in stimulation of MRE11 exonuclease activity |
| XRCC4 | Unknown function; interacts with DNA ligase IV |
| XRCC5 | Ku80; forms heterodimer with Ku70 which binds to DS DNA ends and DS/SS DNA junctions |
| XRCC6 | Ku70; forms heterodimer with Ku 70; deficiency correlated with elevated frequency of T-cell lymphoma |
| XRCC7 | DNA-protein kinase; regulates Ku heterodimer |

The DNA-dependent protein kinase (DNA-PK) consists of the catalytic subunit (DNA-PKcs) and the regulatory subunit (the Ku70/Ku80 heterodimer). The DNA-PKcs subunit is a serine/threonine kinase which belongs to the phosphatidyl inositol-3 kinase family. The Ku80/Ku70 heterodimer (Ku) exhibits sequence-independent affinity for double-stranded termini and, upon binding to DNA, recruits and activates the DNA-PKcs catalytic subunit. Several candidate inhibitors of the DNA-PK have been described, for example viridins (Hanson, J. R. Nat. Prod. Rep., 12: 381-384, 1995), wortmannin, quercitins (Izzard et al. (1999) *Cancer. Res.*, 59: 2581-2586), LY294002 (Vlahos et al. (1994) *J. Biol. Chem.*, 269: 5241-5248), which are incorporated herein by reference. Other inhibitors of NHEJ include inhibitors of ATM disclosed within U.S. Ser. No.2004/0002492, which are incorporated herein by reference.

B. Base Excision Repair (BER)

Single Strand DNA breaks (SSBs) are one of the most frequent lesions occurring in cellular DNA. SSBs can occur spontaneously or as intermediates of enzymatic repair of base damage during Base Excision Repair (BER) (Caldecott (2001) *Bioessays* 23(5): 447-55). In this repair pathway, which follows the removal of a damaged base by a DNA glycosylase, the resulting apurinic/apyrimidinic (AP) site is processed first by the Ape1 AP endonuclease, leaving a 5' deoxyribose-phosphate; then by an AP lyase activity leaving a 3'β-elimination product. The subsequent removal of these AP sites by DNA Polymerase β, or by a PCNA-dependent polymerase, allows the repair synthesis to fill-in either a single nucleotide (for Pol β) or a longer repair patch (for Pol δ/ε), which are then re-ligated (Wilson (1998) *Mutat Res.* 407:203-15). If SSB sites are not efficiently processed and removed, clusters of damaged sites and stalled replication forks will form, resulting in the formation of DSBs with potentially lethal consequences for the cell (Chaudhry & Weinfeld (1997) *J Biol Chem.* 272:15650-5; Harrison, Hatahet et al. (1998) *Nucleic Acids Res.* 26:932-41).

Poly(ADP-ribose) polymerase (PARP) is a DNA binding zinc finger protein that catalyzes the transfer of ADP-ribose residues from NAD+ to itself and different chromatin constituents, forming branched ADP-ribose polymers. The enzymatic activity of PARP is induced upon DNA damage, suggesting a role of PARP in DNA repair and DNA damage-induced cell death. Numerous inhibitors of PARP have been disclosed, some of which are commercially available. For example, PJ-34 N-(6-oxo-5,6-dihydrophenanthridin-2-yl)-N,N-dimethylacetamide.Hcl, INHBP 5-iodo-6-amino-1,2-benzopyrone, 3-Aminobenzamide, Benzamide, 4-Amino-1,8-naphthalimide, 6(5H)-Phenanthridinone, 5-Aminoisoquinolinone (5-AIQ). hydrochloride, 4-Hydroxyquinazoline, 4-Quinazolinol, 1,5-Isoquinolinediol, 5-Hydroxy-1(2H)-isoquinolinone, 3,4-Dihydro-5-[4-(1-piperidinyl)butoxy]-1 (2H)-isoquinolinone (DPQ) are all available from Inotek Pharmaceuticals (Beverly, Mass.). Other compounds, such as GPI 15427 (Tentori et al. (2003) *Proceedings of the AACR*, 44, Abs No. 5466) and methoxyamine (Liuzzi et al., (1985) *J. Biol. Chem.* 260, 5252-5258; Rosa et al. (1991) *Nucleic Acids Res.*, 19, 5569-5574; and Horton et al. (2000) *J. Biol. Chem.*, 275, 2211-2218) have been reported to enhance the anti-neoplastic efficacy of both chemotherapy and radiation therapy.

C. Nucleotide Excision Repair (NER)

Nucleotide excision repair (NER) acts on a variety of helix-distorting DNA lesions, caused mostly by exogenous sources that interfere with normal base pairing. The primary function of NER in man appears to be the removal of damage, for example pyrimidine dimers, which are induced by ultraviolet light (UV). Members of the NER pathway, defects of which can cause an autosomal recessive disease called xeroderma pigmentosum (XP), have been identified, including seven different genes, XPA, XPB, XPC, XPD, XPE, XPF and XPG, all of which function in the NER pathway (Hoeijmakers (2001) *Mutat Res.* 485:43-59).

Eukaryotic NER includes two major branches, transcription-coupled repair (TCR) and global genome repair (GGR) (de Laat et al. (1999) *Genes Dev.* 13:768-85, Tornaletti & Hanawalt (1999) *Biochimie.* 81:139-46). GGR is a slow random process of inspecting the entire genome for injuries, while TCR is highly specific and efficient and concentrates on damage-blocking RNA polymerase II. The two mechanisms differ in substrate specificity and recognition. In GGR, the XPC-HR23B complex recognizes damage located in non-transcribed regions (Sugasawa et al. (2001) *Genes Dev.* 15:507-21), whereas the arrest of RNA polymerase II (RNAPII) serves as the recognition signal in TCR. The molecular mechanism of RNAPII displacement is currently unclear, but essential factors, such as the Cocayne's syndrome proteins CSA, CSB, XPA-binding protein 2 (XAB2), TFIIH and XPG (Svejstrup 2002), have been identified to function in TCR. Subsequently, both in GGR and TCR, an open unwound structure forms around the lesion. This creates specific cutting sites for XPG and ERCC1-XPF nucleases, and the resulting gap is filled in by PCNA-dependent polymerase and sealed by DNA ligase (de Laat et al., id).

D. Mismatch Repair (MR)

Mismatch repair (MMR) removes both nucleotides mispaired by DNA polymerases and insertion/deletion loops caused by slippage during replication of repetitive sequences (Harfe & Jinks-Robertson (2000) *Annu Rev Genet* 34: 359-399). Initially, the heterodimeric MSH complex recognizes the nucleotide mismatch, subsequently followed by interaction with MLH1/PMS2 and MLH1/MLH3 complexes. Several proteins participate in process of the nucleotide excision and resynthesis. Tumor cells deficient in mismatch repair have much higher mutation frequencies than normal cells (Parsons et al. (1993) *Cell* 75: 1227-1236, Bhattacharyya et al. (1994) *Proc Natl Acad. Sci USA* 91: 6319-6323). At least six genes MSH2, MLH1, PMS2, MSH3, MSH6 and MLH3 have been identified in humans which are involved in mismatch repair. Defects in these genes except for MSH3 leads to hereditary nonpolyposis colon cancer (HNPCC) (Hoeijmakers 2001).

Other inhibitors to DNA damage repair have been disclosed, including aphidicolin, (Gera (1993) *J Immunol.* 151: 3746-57), rapamycin (mTOR inhibitor, Sabers et al., (1995) *J Biol. Chem.* 270:815-22), the AGT inhibitor 06-benzylguanine (Bronstein et al., (1992) *Cancer Res.* 52:3851-6).

VII. Identifying Inhibitors of Non-FA DNA Damage Repair Pathways.

As previously described, in certain situations the DNA damage repair pathways of the cell can be partially redundant. This presents difficulties in identifying agents which specifically block one pathway. Inhibitors identified using cell-based methods wherein the cells have functional DNA damage repair pathways may therefore have multiple targets, including in a plurality of DNA damage repair pathways. Therefore, use of cell lines deficient in one or more DNA damage repair pathways may greatly accelerate the identification of novel, specific inhibitors. Therefore, according to one aspect, a method of identifying agents which inhibit a non-FA DNA damage repair pathway is provided. The method employs cells which have a lesion in the FA pathway. The method comprises contacting cells with an agent, and testing for sensitivity to a genotoxic anti-neoplastic agent. An agent which confers enhanced sensitivity to the genotoxic anti-neoplastic agent in test cells containing a lesion in the FA pathway when compared with control cells containing functional DNA damage repair pathways indicates that the agent inhibits a non-FA DNA damage repair pathway other than the pathway in which the test cell contains a lesion. In one embodiment, test and control cells are isogenic, except that the test cell contains a lesion in at least one component of the FA/BRCA pathway, for example, in FANCA, FANCB, FANCC, FANCD FANCE FANCF FANCG FANCL, and the ATR protein kinase, among others.

According to one embodiment, the method comprises comparing the sensitivities to genotoxic anti-neoplastic agents of two isogenic cell lines which differ in the functionality of the FA pathway. In one embodiment, two isogenic ovarian tumor lines, a parental 2008 and the 2008 cells complemented with the FANCF cDNA, are employed. The parental 2008 cells fail to express FANCF, these cells have a disruption of the FA pathway, and they are hypersensitive to cisplatin. Complementation of the 2008 cells with the FAN CF cDNA restores FA pathway in these cells. Therefore, these control cells therefore serve as a basis for comparison. This isogenic pair of cells is subjected to a high throughput chemical screen with a library of compounds, for example kinase inhibitors. Agents which selectively kill 2008 cells (lacking the FA/BRCA pathway) but which do not kill the corrected 2008 plus FANCF control cells are candidate inhibitors of a non-FA DNA damage repair pathway.

The availability of these isogenic cell lines also permits the identification of gene products which are involved in DNA damage repair pathways other than the FA pathway. In one embodiment, genes affecting the viability of the parental but not the control cells are tested by systematic, mass inhibition using an siRNA library. For example, a bar-coded siRNA library can be used to for stable transfection of the two cell lines. Genes that are required for viability of the 2008 cells, but not for the corrected cells. Genes which are important for DNA damage repair pathways other than the FA pathway, for example in the BER pathway, is expected to have the result that siRNA knockdown of such a gene will be lethal in the parental 2008 cells, but not in the control 2008 cells which have been transfected with the FANCF cDNA.

Agents thus identified which can kill a cell in which one or more DNA damage repair pathways is disrupted but do not kill an isogenic cell line in which the disruption is restored can be used in the treatment of cancer. Disruption of two or more of the six major DNA damage repair pathways can result in cell death. Since many cancers already have the one pathway knocked out or repressed, a relatively non-toxic inhibitor of the second pathway, for example the BER pathway, may be sufficient to cause cytoreduction of the cancer, even in the absence of a chemotherapeutic agent. In addition, in tumors cells in which the major DNA damage repair pathways are intact, using two inhibitors in combination (e.g., one inhibitor of the FA pathway and one inhibitor of the BER pathway) may be sufficient to cause significant cytoreduction, provided that the toxicity of such a combination is not toxic to normal (non-cancer) cells. In such a case, a pro-drug strategy to enhance uptake of these agents by cancer cells provide the necessary therapeutic index.

VIII. Anti-Neoplastic Agents

Disclosed herein are methods of treating patients with neoplastic disorders using a combination of anti-neoplastic agents in combination with inhibitors of DNA damage repair pathways. Anti-neoplastic agents which are particularly useful include, but are not limited to, agents which cause damage to the DNA. These agents include DNA alkylating agents, intercalating agents, and the like. Further contemplated, therefore, is the use of DNA-damaging chemotherapeutic compounds including, but not limited to, 1,3-Bis(2-Chloroethyl)-1-NitrosoUrea (BCNU), Busulfan, Carboplatin, Carmustine, Chlorambucil, Cisplatin, Cyclophosphamide, Dacarbazine, Daunorubicin, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide, and Topotecan. Furthermore, methods described herein can also employ radiotherapeutic methods of treating neoplastic disorders. In one embodiment, the genotoxic anti-neoplastic agents do not inhibit DNA damage repair at the concentrations administered.

IX. Identifying Responders to Anti-neoplastic Agents

The present invention is based on the surprising discovery that the efficacy of the FA pathway of a cell strongly correlates with its sensitivity to chemotherapeutic agents. Therefore, in one aspect, the invention provides a method of predicting whether a subject with a neoplastic disorder or disease will respond to a genotoxic anti-neoplastic agent. The method comprises obtaining a biological sample from the subject, and determining degree of ubiquitination of the Fanconi anemia complementation group D2 (FANC D2) polypeptide within the biological sample. A degree of ubiquitination of the FANC D2 polypeptide in the biological sample of the subject that is less than about 70% when compared with a biological sample from a control subject is indicative of a subject that will respond to a genotoxic anti-neoplastic agent.

In another aspect, the invention provides a method of predicting whether a subject with a neoplastic disorder or disease will respond to a genotoxic anti-neoplastic agent. The method comprises obtaining a biological sample from the subject, and determining the FANC D2-containing foci within the biological sample. A difference in foci formation, wherein the sample from the subject that contains less than about 70% of the FANC D2-containing foci when compared with the biological sample from a control subject is indicative of a subject that will respond to a genotoxic anti-neoplastic agent.

In one embodiment, the neoplastic disorder is selected from the group consisting of leukemia, acute myeloid leukemia, chronic myeloid leukemia, chronic lymphatic leukemia, myelodysplasia, multiple myeloma, Hodgkin's disease or non-Hodgkin's lymphoma, small or non-small cell lung carcinoma, gastric, intestinal or colorectal cancer, prostate, ovarian or breast cancer, head, brain or neck cancer, cancer in the urinary tract, kidney or bladder cancer, malignant melanoma, liver cancer, uterine or pancreatic cancer.

According to these aspects, the ability of a biological sample to activate the FA pathway, as determined by measuring the level of FANC D2 monoubiquitination, is determined to identify responders to chemotherapeutic agents, particularly genotoxic anti-neoplastic agents. The anti-neoplastic agents can be any which are used for the treatment of cancer, and in one embodiment, anti-neoplastic agents' mechanism of action is through the damage of DNA. These compounds include but are not limited to: 1,3-Bis(2-Chloroethyl)-1-NitrosoUrea (BCNU), Busulfan, Carboplatin, Carmustine, Chlorambucil, Cisplatin, Cyclophosphamide, Dacarbazine, Daunorubicin, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide, and Topotecan and ionizing radiation.

In certain embodiments the patient or, alternatively, the biological sample obtained from the patient, can be exposed to the anti-neoplastic agent prior to determining the degree of ubiquitination of the FANC D2 polypeptide. In one embodiment, the patient or biological sample obtained from the subject is exposed at a dose that is less than or equal to the therapeutically effective dose. In another embodiment, the exposure is at 50% or less of the therapeutically. effective dose of the anti-neoplastic agent.

The degree of ubiquitination of the FANC D2 polypeptide can be compared with that of a control subject. As used herein, a control subject can be a single subject that has previously been determined to be normal with respect to response to anti-neoplastic agents, or a number of normal subjects. Biological samples from either a single control subject or a number of control subjects can be used. In this aspect, a subject is deemed to be a responder to an anti-neoplastic agent if the percentage of FANC D2 ubiquitination is less than about 70% when compared with a sample from a subject, for example, less than 70%, less than 65%, less than 60%, less than 50%, less than 40%, less than 30%, less than 20%, less than 10% or less, when compared with a sample from a subject that has received the same or equivalent dose of anti-neoplastic agent as the test sample. Furthermore, in embodiments involving exposure to an anti-neoplastic agent prior to determining the degree of ubiquitination of the FANC D2 polypeptide, control samples can be prepared prior to preparation of the test samples, or prepared simultaneously to preparation of the test samples.

In one embodiment, the subject, or alternatively the biological sample taken from the subject, can be treated with a genotoxic anti-neoplastic agent prior to measurement of the efficacy of the FA pathway. The dosage of the anti-neoplastic agent would be that necessary to induce the FA pathway in a normal subject. Typically, the dosage of the anti-neoplastic agent would be from between about 5% to 100% of the typical therapeutically effective dose, more typically between 20% to 100%, and most typically between about 35%-100%.

As described herein, there are a number of ways in which to measure the degree of ubiquitination of the FANC D2 polypeptide in biological samples. The degree of ubiquitination of the FANC D2 polypeptide can be measured using immunoblot analysis as previously described. Alternatively, one could detect the formation of FANC D2-containing foci, for example using immunofluorescence microscopy of biological samples, as a surrogate marker for FANC D2 ubiquitination.

Subjects are considered responders if the formation of ubiquitinated FANC D2 polypeptide is about 70% or less when compared with normal subjects, for example 70% or less, 65% or less, 60% or less, 50% or less, 40% or less, 30% or less than in normal subjects.

X. Treatment of Neoplastic Disorders

In certain embodiments, a subject or patient is administered with a therapeutically effective dose of a genotoxic anti-neoplastic agent, simultaneously, before or after administration with an inhibitor of a non-FA DNA damage repair pathway, for example the FA pathway. Therapeutically effective dosages of many anti-neoplastic agents are well-established, and can be found, for example, in Cancer Chemotherapy and Biotherapy: A Reference Guide Edition Number: 2 Tenenbaum, ed. Saunders & CO (1994) which is incorporated herein by reference.

Also provided herein are methods for treating a neoplastic disorder in a subject in need thereof. In one aspect, the method comprises administering to the subject an effective amount of an inhibitor of the FA pathway and a genotoxic anti-neoplastic agent. The anti-neoplastic agent can be selected from the group consisting of 1,3-Bis(2-Chloroethyl)-1-NitrosoUrea (BCNU), Busulfan, Carboplatin, Carmustine, Chlorambucil, Cisplatin, Cyclophosphamide, Dacarbazine, Daunorubicin, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide, and Topotecan and ionizing radiation.

In another aspect, a method of treating a neoplastic disorder in a subject in need thereof is provided. The method comprises administering to the subject an effective amount of an inhibitor of the FA pathway and an inhibitor of a non-FA DNA damage repair pathway. The inhibitor of a non-FA DNA damage repair pathway can be selected which inhibits any of the repair pathways, and can be selected from the group consisting of PARP inhibitors, DNA-PK inhibitors, mTOR inhibitors, ERCC1 inhibitors ERCC3 inhibitors, ERCC6 inhibitors, ATM inhibitors, XRCC4 inhibitors, Ku80 inhibitors, Ku70 inhibitors, XPA inhibitors, CHK1 inhibitors, CHK2 inhibitors, or pharmaceutically acceptable salts, esters, derivatives, solvates or prodrugs thereof. The inhibitor of the FA pathway can be administered before, simultaneously with, or after administration of the inhibitor of the non-FA DNA damage repair pathway. The inhibitors can be administered parenterally, orally or directly into the tumor.

The inhibitor of the FA pathway, as well as inhibitor of a non-FA DNA damage repair pathway, can act to increase the sensitivity of a neoplastic disorder to a genotoxic anti-neoplastic agent. Therefore, in another aspect, a method of increasing the sensitivity of a neoplastic disorder to a genotoxic anti-neoplastic agent is provided. The method comprises administering before, after or concurrently with a therapeutically effective dose of the agent a combination of an effective amount of an inhibitor of the FA pathway and an inhibitor of a non-FA DNA damage repair pathway. The method can be useful for the treatment of many types of neoplastic disorders, and can be selected from the group consisting of leukemia, acute myeloid leukemia, chronic myeloid leukemia, chronic lymphatic leukemia, myelodysplasia, multiple myeloma, Hodgkin's disease or non-Hodgkin's lymphoma, small or non-small cell lung carcinoma, gastric, intestinal or colorectal cancer, prostate, ovarian or breast cancer, head, brain or neck cancer, cancer in the urinary tract, kidney or bladder cancer, malignant melanoma, liver cancer, uterine or pancreatic cancer.

The inhibitors of the FA pathway are further useful as agents which increase the sensitivity of a neoplastic disorder to a genotoxic anti-neoplastic agent. Therefore, in another aspect, the invention provides a method of increasing the sensitivity of a neoplastic disorder to a genotoxic anti-neoplastic agent. The method comprises administering before, after or concurrently with a therapeutically effective dose of an genotoxic anti-neoplastic agent, an effective amount of an inhibitor of the FA pathway. As previously described, the inhibitor of the FA pathway can be administered before, simultaneously with, or after administration of the inhibitor of the non-FA DNA damage repair pathway, and can be administered parenterally, orally or directly into the tumor. In one embodiment, the method further comprises administering an inhibitor of a non-FA DNA damage repair pathway, in addition to the FA inhibitor and genotoxic anti-neoplastic agent. The inhibitor of the non-FA DNA damage repair pathway can be administered before, after, or concurrently with a therapeutically effective dose of the FA pathway inhibitor and genotoxic anti-neoplastic agent.

The efficacy of compositions disclosed herein in preventing or treating neoplastic disorders can be tested, for example, in animal models of specific neoplastic disorders. Numerous examples of animal models are well known to those skilled in the art, and are disclosed, for example, in Holland, Mouse Models of Cancer (Wiley-Liss 2004); Teicher, Tumor Models in Cancer Research (Humana Press; 2001); Kallman, Rodent Tumor Models in Experimental Cancer Therapy (Mcgraw-Hill, TX, 1987); Hedrich, The Laboratory Mouse (Handbook of Experimental Animals) (Academic Press, 2004); and Arnold and Kopf-Maier, Immunodeficient Animals: Models for Cancer Research (Contributions to Oncology, Vol 51) (Karger, 1996), the contents of which are incorporated herein in their entirety.

XI. Test Compounds According to the Invention Whether in an in vitro or in vivo system, the invention encompasses methods by which to screen compositions which can inhibit the formation of FANC D2-containing foci, as well as compositions which inhibit DNA damage repair pathways other than the FA pathway. Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 Daltons, preferably less than about 750, more preferably less than about 350 Daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g., for the amino group, acylation or alkylation, and for the carboxyl group, esterification or amidification, or the like.

Candidate modulators which may be screened according to the methods of the invention include receptors, enzymes, ligands, regulatory factors, and structural proteins. Candidate modulators also include nuclear proteins, cytoplasmic proteins, mitochondrial proteins, secreted proteins, plasmalemma-associated proteins, serum proteins, viral antigens, bacterial antigens, protozoan antigens and parasitic antigens. Candidate modulators additionally comprise proteins, lipoproteins, glycoproteins, phosphoproteins and nucleic acids (e.g., RNAs such as ribozymes or antisense nucleic acids). Proteins or polypeptides which can be screened using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens, bacterial antigens and antibodies (see below).

Candidate modulators which may be screened according to the invention also include substances for which a test cell or organism might be deficient or that might be clinically effective in higher-than-normal concentration as well as those that are designed to eliminate the translation of unwanted proteins. Nucleic acids of use according to the invention not only may encode the candidate modulators described above, but may eliminate or encode products which eliminate deleterious proteins. Such nucleic acid sequences are antisense RNA and ribozymes, as well as DNA expression constructs that encode them. Note that antisense RNA molecules, ribozymes or genes encoding them may be administered to a test cell or organism by a method of nucleic acid delivery that is known in the art, as described below. Inactivating nucleic acid sequences may encode a ribozyme or antisense RNA specific for the target mRNA. Ribozymes of the hammerhead class are the smallest known, and lend themselves both to in vitro production and delivery to cells (summarized by Sullivan, (1994) *J. Invest. Dermatol.*, 103: 85S-98S; Usman et al., (1996), *Curr. Opin. Struct. Biol.*, 6: 527-533).

XII. Pharmaceutical Compositions

In another aspect, the invention relates to methods and pharmaceutical compositions comprising an inhibitor of the FA pathway in combination with an anti-neoplastic agent and/or inhibitor of a non-FA DNA damage repair pathway, as described in the preceding section, and a pharmaceutically acceptable carrier, as described below. The pharmaceutical composition comprising an inhibitor of the FA pathway is useful for treating a variety of diseases and disorders including cancer, and may be useful as protective agents against genotoxic anti-neoplastic agents.

In one embodiment, the invention provides for a method of treating a neoplastic disorder in a subject in need thereof comprising administering a combination of an effective amount of:

a) an inhibitor of the FA pathway or pharmaceutically acceptable salts, esters, derivatives, solvates or prodrugs thereof, and b) a genotoxic anti-neoplastic agent.

Examples of inhibitors of the FA pathway include H-9, alsterpaullone and curcumin. However, it will be appreciated by those skilled in the art that additional inhibitors of the FA pathway can be identified, for example, using the methods described herein. In this regard, an inhibitor of the FA pathway can be a small molecule, and antibody, a ribozyme or siRNA molecule.

The method can be used in the treatment of various neoplastic disorders, including leukemia, acute myeloid leukemia, chronic myeloid leukemia, chronic lymphatic leukemia, myelodysplasia, multiple myeloma, Hodgkin's disease or non-Hodgkin's lymphoma, small or non-small cell lung carcinoma, gastric, intestinal or colorectal cancer, prostate, ovarian or breast cancer, head, brain or neck cancer, cancer in the urinary tract, kidney or bladder cancer, malignant melanoma, liver cancer, uterine or pancreatic cancer. In one embodiment, the method is used to treat ovarian cancer.

The dosage of the inhibitor of the FA pathway depends on several factors, including solubility, bioavailability, plasma protein binding, kidney clearance, and inhibition constants. In certain therapeutic applications, an adequate amount to accomplish at least partial inhibition of the FA pathway is defined as an "effective dose". Amounts needed to achieve this dosage will depend upon the severity of the disease and the general state of the patient's own immune system, but generally range from 0.005 to 5.0 mg of the inhibitor per kilogram of body weight, with doses of 0.05 to 2.0 mg/kg/dose being more commonly used. Alternatively, the dosage can be administered using a functional dosage, since the activation of the FA pathway in a subject can be determined empirically using the ubiquitination of the FANC D2 polypeptide using the methods described herein. Therefore, an "effective dose" of an inhibitor of the FA pathway can mean a dose required to reduce the level of FANC D2 ubiquitination to about 70% or less when compared with a control sample, more typically to about 50% or less than a control sample. In this regard, a control sample is ideally taken from the same subject, before administration of the inhibitor.

The dosage of the inhibitor of the FA pathway in relation to the dosage of the genotoxic anti-neoplastic agent can be expressed as a ratio. The inhibitor of the FA pathway can be administered at a ratio of between about 100:1 to about 1:100, on a molar basis, in relation to the genotoxic anti-neoplastic agent, for example, at 1:100, 1:50, 1:10, 1:5, 1:2, 1:1, 2:1, 5:1, 10:1, 20:1, 50:1, or 100:1.

The genotoxic anti-neoplastic agent are agents which are used to treat neoplastic disorders, and include 1,3-Bis(2-Chloroethyl)-1-NitrosoUrea (BCNU), Busulfan, Carboplatin, Carmustine, Chlorambucil, Cisplatin, Cyclophosphamide, Dacarbazine, Daunorubicin, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide, and Topotecan.

Dosages of the anti-neoplastic agents listed above have been well established for different types of neoplastic disorders. However, co-administration with inhibitors of the FA pathway can increase the sensitivity of the neoplastic disorders to the anti-neoplastic agents. Therefore, it is possible that the dosage of the anti-neoplastic agents will be less than is typically administered for the given neoplastic disorder. The lower dosage may have the additional advantage of reduced side effects. However, typically, the dosage of the anti-neoplastic agent is expected to be within about 20%-100% of the typical dosage for the given neoplastic disorder, more typically between about 35%-100%.

In yet another embodiment, the present invention provides for a method of treating a neoplastic disorder in a subject in need thereof, comprising administering to the subject a combination of an effective amount of:

(a) an inhibitor of the FA pathway or pharmaceutically acceptable salts, esters, derivatives, solvates or prodrugs thereof, and (b) an inhibitor of a DNA damage repair pathway.

The inhibitor of a DNA damage repair pathway can be selected from the group consisting of PARP inhibitors, DNA-PK inhibitors, FA inhibitors, mTOR inhibitors, ERCC1 inhibitors, ERCC3 inhibitors, ERCC6 inhibitors, ATM inhibitors, XRCC4 inhibitors, Ku80 inhibitors, Ku70 inhibitors, XPA inhibitors, CHK1 inhibitors, CHK2 inhibitors, or pharmaceutically acceptable salts, esters, derivatives, solvates or prodrugs thereof.

In one embodiment, the non-FA DNA damage repair pathway is a pathway other than the FA pathway. In one embodiment, the inhibitor targets a pathway selected from the group consisting of the non-homologous end joining DNA damage repair pathway, the mismatch repair pathway, and the nucleotide excision pathway. In another embodiment, the inhibitor targets the non-homologous end joining DNA damage repair pathway. In yet another embodiment, the inhibitor targets the direct reversal pathway. In another embodiment, the inhibitor targets the mismatch repair pathway. In still another embodiment, the inhibitor targets the nucleotide excision repair pathway. In another embodiment, the inhibitor targets the base excision repair pathway.

Ideal dosages of the inhibitor of a DNA damage repair pathway, as described above for inhibitors of the FA pathway, will depend upon the severity of the disease and the general state of the patient's own immune system, but generally range from 0.005 to 5.0 mg of the inhibitor per kilogram of body weight, with doses of 0.05 to 2.0 mg/kg/dose being more commonly used. Alternatively, the appropriate dosage can be determined empirically, inhibition of DNA damage repair pathways can be measured using biological samples taken from the subject. Therefore, an "effective dose" of an inhibitor of the DNA damage repair pathway can mean a dose required to reduce the level of the specific pathway to about 70% or less when compared with a control sample, more typically to about 50% or less than a control sample. In this regard, a control sample is ideally taken from the same subject, before administration of the inhibitor.

In yet another embodiment, the present invention provides for a method of treating a neoplastic disorder in a subject in need thereof, comprising administering to said subject a combination of an effective amount of:

(a) an inhibitor of the FA pathway or pharmaceutically acceptable salts, esters, derivatives, solvates or prodrugs thereof, (b) an inhibitor of a non-FA DNA damage repair pathway, and (c) a genotoxic anti-neoplastic agent or pharmaceutically acceptable salts, esters, derivatives, solvates or prodrugs thereof.

The inhibitor of the FA pathway, its dosage and method of administration, are as described previously. Likewise, the inhibitor of a non-FA DNA damage repair pathway, as well as its dosage and method of administration are the same as previously described. However, as previously described, administration of inhibitors of the FA pathway, as well as of a non-FA DNA damage repair pathway, can heighten the sensitivity to a genotoxic anti-neoplastic agent. Therefore, it is possible that the dosage of the anti-neoplastic agents will be less than is typically administered for the given neoplastic disorder. The lower dosage may have the additional advantage of reduced side effects. However, typically, the dosage of the anti-neoplastic agent is expected to be within about 20%-100% of the typical dosage for the given neoplastic disorder, more typically between about 35%-100%.

The compounds of the present invention, or pharmaceutically acceptable salts, esters, derivatives, solvates or prodrugs thereof, can be formulated for oral, intravenous, intramuscular, subcutaneous, topical and/or parenteral administration for the therapeutic or prophylactic treatment of diseases. For oral or parental administration, compounds of the present invention can be mixed with conventional pharmaceutical carriers and excipients and used in the form of tablets, capsules, elixirs, suspensions, syrups, wafers and the like. The compositions comprising a compound of this present invention will contain from about 0.1% to about 99.9%, about 1% to about 98%, about 5% to about 95%, about 10% to about 80% or about 15% to about 60% by weight of the active compound.

The compounds of the present invention can be administered at separate times, using separate methods of administration. For example, in certain situations, it may be advantageous to administer the inhibitor of the FA pathway before, simultaneously with, or after administration of the genotoxic anti-neoplastic agent or other agents. Likewise, the method of administration of each compound will depend on the optimal means of administration thereof.

The pharmaceutical preparations disclosed herein are prepared in accordance with standard procedures and are administered at dosages that are selected to reduce, prevent, or eliminate cancer, or to provide a protective effect against genotoxic anti-neoplastic agents such as ionizing radiation. (See, e.g., *Remington's Pharmaceutical Sciences*, Mack Publishing Company, Easton, Pa.; and Goodman and Gilman, *Pharmaceutical Basis of Therapeutics*, Pergamon Press, New York, N.Y., the contents of which are incorporated herein by reference, for a general description of the methods for administering various antimicrobial agents for human therapy). The compositions of the present invention can be delivered using controlled (e.g., capsules) or sustained release delivery systems (e.g., biodegradable matrices). Examples of delayed release delivery systems for drug delivery suitable for administering compositions of the invention are described in U.S. Pat. No. 4,452,775, U.S. Pat. No. 5,239,660, and U.S. Pat. No. 3,854,480.

The pharmaceutically acceptable compositions of the present invention comprise one or more compounds of the present invention in association with one or more non-toxic, pharmaceutically acceptable carriers and/or diluents and/or adjuvants and/or excipients, collectively referred to herein as "carrier" materials, and if desired other active ingredients. The compositions may contain common carriers and excipients, such as corn starch or gelatin, lactose, sucrose, microcrystalline cellulose, kaolin, mannitol, dicalcium phosphate, sodium chloride and alginic acid. The compositions may contain crosarmellose sodium, microcrystalline cellulose, sodium starch glycolate and alginic acid.

Tablet binders that can be included are acacia, methylcellulose, sodium carboxymethylcellulose, polyvinylpyrrolidone (Providone), hydroxypropyl methylcellulose, sucrose, starch and ethylcellulose.

Lubricants that can be used include magnesium stearate or other metallic stearates, stearic acid, silicon fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product comprising a compound of the present invention.

For oral use, solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica or talc: disintegrants, for example, potato starch, flavoring or coloring agents, or acceptable wetting agents. Oral liquid preparations generally are in the form of aqueous or oily solutions, suspensions, emulsions, syrups or elixirs and may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl parahydroxybenzoate, propylene glycol, sorbitol, or sorbic acid.

For intravenous (iv) use, compounds of the present invention can be dissolved or suspended in any of the commonly used intravenous fluids and administered by infusion. Intravenous fluids include, without limitation, physiological saline or Ringer's solution.

Formulations for parental administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For intramuscular preparations, a sterile formulation of compounds of the present invention or suitable soluble salts forming the compound, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g. an ester of a long chain fatty acid such as ethyl oleate.

For topical use the compounds of present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compound of the present invention can be in powder form for reconstitution in the appropriate pharmaceutically acceptable carrier at the time of delivery. In another embodiment, the unit dosage form of the compound can be a solution of the compound or a salt thereof in a suitable diluent in sterile, hermetically sealed ampoules.

The amount of the compound of the present invention in a unit dosage comprises a therapeutically-effective amount of at least one active compound of the present invention which may vary depending on the recipient subject, route and frequency of administration. A subject refers to an animal such as an ovine or a mammal, including a human.

According to this aspect of the present invention, the novel compositions disclosed herein are placed in a pharmaceutically acceptable carrier and are delivered to a recipient subject (including a human subject) in accordance with known methods of drug delivery. In general, the methods of the invention for delivering the compositions of the invention in vivo utilize art-recognized protocols for delivering the agent with the only substantial procedural modification being the substitution of the compounds of the present invention for the drugs in the art-recognized protocols.

The compounds of the present invention provide a method for treating pre-cancerous or cancerous conditions, or for use as a protective agent against genotoxic anti-neoplastic agents. As used herein, the term "unit dosage" refers to a quantity of a therapeutically effective amount of a compound of the present invention that elicits a desired therapeutic response. The term "treating" is defined as administering, to a subject, a therapeutically effective amount of at least one compound of the present invention, both to prevent the occurrence of a pre-cancer or cancer condition, or to control or eliminate pre-cancer or cancer condition. The term "desired therapeutic response" refers to treating a recipient subject with a compound of the present invention such that a pre-cancer or cancer condition is reversed, arrested or prevented in a recipient subject.

The compounds of the present invention can be administered as a single daily dose or in multiple doses per day. The treatment regime may require administration over extended periods of time, e.g., for several days or for from two to four weeks. The amount per administered dose or the total amount administered will depend on such factors as the nature and severity of the disease condition, the age and general health of the recipient subject, the tolerance of the recipient subject to the compound and the type of cancer, the sensitivity of the cancer to therapeutic agents, and, if used in combination with other therapeutic agent(s), the dose and type of therapeutic agent(s) used.

A compound according to this invention may also be administered in the diet or feed of a patient or animal. The diet for animals can be normal foodstuffs to which the compound can be added or it can be added to a premix.

The compounds of the present invention may be taken in combination, together or separately with any known clinically approved agent to treat a recipient subject in need of such treatment.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Further disclosure relevant to the methods and embodiments described herein can be found in Chirnomas et al., Mol. Cancer Ther. 5(4):952-961 (2006) and Taniguchi and D'Andrea, published electronically in Blood (2006) at DOI 10.1182/blood-2005-10-4240, both of which are incorporated by reference in their entirety. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Methods

Cell Lines and Cell Culture.

HeLa cells, PD20 (FA-D2) fibroblasts, and GM6914 (FA-A) fibroblasts were grown as previously described (Taniguchi et al. (2002) *Cell*. 109:459-472). Briefly, cells were grown in Dulbecco's modified eagles medium (DMEM) supplemented with 15% fetal calf serum (FCS). The FANCF-deficient ovarian tumor line (2008) and FANCF cDNA corrected 2008 cells were previously described. Breast cancer cell line MCF7 was purchased from the American Type Culture Collection (Manassas, Va.). OVCAR5 and OVCAR8 were grown as previously described.

Plasmids and Retroviral Infection

The retroviral expression vector, pMMP-puro (Ory et al., (1996) *Proc Natl Acad. Sci USA*. 93:11400-11406) and pMMP-puro-FANCD2 was described previously (Timmers et al., (2001) *Mol Cell*. 7:241-248; Garcia-Higuera et al., (2001) *Mol Cell*. 7:249-262). pMMPpuro EGFP-FANCD2 was constructed by adding EGFP cDNA sequence (from pEGFP-N1 (Clontech)) to the N-terminus of the FANCD2 cDNA sequence. The cDNA insert was verified by direct DNA sequencing. Production of pMMP retroviral supernatants and infection of fibroblasts (PD20 fibroblasts) was performed as previously described (Naf et al., (1998) *Mol Cell Biol*, 18:5952-5960). After 48 hours, cells were trypsinized and selected in medium containing puromycin (1 µg/mL). Dead cells were removed, and surviving cells were grown under continuous selection in puromycin. Subcloning of PD20 fibroblasts infected with pMMPpuroEGFP-FANCD2 was performed by limited dilution, and a clone which showed clear EGFP-FANCD2 foci formation in response to IR treatment (15Gy, 10 hr) was selected (PD20F-EGFP-FANCD2 clone 7) for the drug screening study.

Cytotoxicity Assays.

Human cells (HeLa cells, PD20 fibroblasts, or 2008 cells, where indicated; Taniguchi et al., (2003) *Nat Med*. 9:568-574) were seeded onto 12-well plates at $9 \times 10^4$ cells/well in DMEM-15% FCS (5 ml). After cells attached for 16 to 24 h, the medium was replaced with DMEM-15% FCS containing cisplatin (CDDP) or MMC (Sigma) at various concentrations, with or without a kinase inhibitor or curcumin (Sigma) at either variable or the same concentration. The cells were incubated at 37° C. for one day. The media was removed and the wells were washed once with phosphate-buffered saline (PBS) before the addition of fresh DMEM-15% FCS. After incubation for 5 to 6 days, monolayers were washed twice with (PBS) before and fixed for 5 to 10 min at 23° C. in 10% (vol/vol) methanol and 10% (vol/vol) acetic acid. Adherent colonies were stained for 2 to 10 min at 23° C. with 1% (wt/vol) crystal violet (Sigma) in methanol (0.5 ml per well). Plates were rinsed in distilled water, and the adsorbed dye was resolubilized with methanol containing 0.1% (wt/vol) sodium dodecyl sulfate SDS (0.5 ml per well) by gentle agitation for 1 to 4 h at 23° C. Dye solution (150 µl) was transferred to 96-well plates and diluted (1:3) in methanol. Crystal violet concentrations were measured photometrically (595 nm) in a model 3550 microplate reader (Bio-Rad). For quantitation, readings of optical density at 595 nm were normalized to those obtained from untreated cells (concentration of CDDP=0 nM), assumed to yield 100% cell survival.

Immunofluorescence Microscopy.

Cells were seeded onto four-well chamber slides (Falcon) and cultivated for 16 to 24 h. Slides were rinsed with PBS, and adherent cells were fixed for 20 min at 23° C. in paraformaldehyde (4% [wt/vol] in PBS) and permeabilized with Triton X-100 (0.3% [vol/vol] in PBS) for 10 min at 23° C. Staining with primary (affinity-purified anti-FANCD2) and secondary (fluorescein-conjugated goat anti-rabbit) antibodies was for 2 h at 23° C., followed by counterstaining for 5 min at 23° C. with DAPI (4',6-diamidino-2-phenylindole dihydrochloride; 10 µg/ml in PBS; Sigma). Slides were mounted in Vectashield (Vector Laboratories) and analyzed by fluorescence microscopy.

High Throughput Screen for Small Molecule Inhibitors of the FA/BRCA Pathway.

Initially, we transduced PD20 (FA-D2) fibroblasts with the pMMP-GFP-FANCD2-puro retroviral supernatant and twenty individual puromycin resistant colonies were selected. One clone (clone 7) had a low level of expression of GFP-FANCD2 in the nucleus, judged by fluorescence microscopy, but formed bright GFP foci in response to IR (2Gy). Clone 7 was used in subsequent experiments.

For high throughput screens, clone 7 cells were plated in 384 well plates. One hour after plating, a chemical compound, from a commercial library (Kau et al., (2003) *Cancer*

Cell. 4:463-476.), was added to each well, at a single concentration of approximately 20-40 micromolar. Library compounds were added to duplicate plates. After a twelve-hour incubation, the plates were irradiated (15 Gy), and following an additional twelve-hour incubation, cells were fixed for GFP microscopy. Photomicrographs were obtained for each well, and wells with significant (50%) reduction in GFP foci, were identified by visual inspection.

Immunoblotting.

Whole cell lysates were electrophoresed by SDS-PAGE (7% polyacrylamide, bisacrylamide gels for ATR and FANCD2 analysis and 10% for Chk1 and RPA1 analysis). Proteins were transferred to nitrocellulose, blocked, and incubated with primary antibodies as described (Andreassen et al., (2004) *Genes Dev.* 18:1958-1963). Antibodies included anti-FANCD2 (E35, 1:1000; Garcia-Higuera et al., id), anti-ATR (1:1000 Santa Cruz), anti-phospho-S345-Chk1 (1:1000, Cell Signaling), and anti-Chk1 (1:500 Santa Cruz). Membranes were washed, incubated with HRP-linked secondary antibodies (Amersham), and detected by chemiluminescence (Amersham) as described (Taniguchi et al., (2002) *Cell.* 109: 459-472).

In vitro Kinase Assay for ATR.

The in vitro kinase assay with Flag-ATR and kinase-dead Flag-ATR has been previously described (Andreassen et al., id).

Example 2

Identification and Characterization of Potential Inhibitors of FANC D2 Ubiquitination and Foci Formation Using the microscopy methods detailed above, the 489 known bioactive compounds within the collection of the Institute of Chemistry and Cell Biology (ICCB), Harvard Medical, were screened for inhibition of IR-mediated FANC D2 foci formation. A number of positives were identified using the primary screen, which employed high throughput fluorescence microscopy to identify agents which blocked the formation of FANC D2-containing foci upon exposure to ionizing radiation. A number of compounds were identified, as described within Table 2.

TABLE 2

Compounds identified through screen of ICCB Bioactives

| Compound | Known function |
|---|---|
| Alsterpaullone | cdk1/cycB inhibitor |
| (+−)13-HODE | bioactive lipid |
| NIFEDIPINE | calcium channels |
| PENITREM A | potassium channels |
| Geladanamycin | HSP90 inhibitor |
| Go6976 | PKC inhibitor |
| LEUKOTRIENE B3 | bioactive lipid |
| Trichostatin-A | histone deacetylase inhibitor |
| AG-370 | PDGF receptor kinase inhibitor |
| Mitomycin C | DNA crosslinker |
| Amanitin (alpha-amanitin) | transcription inhibitor |
| HNMPA-(AM)3 | Insulin receptor TK inhibitor |
| Propidium iodide | DNA intercalator |
| DRB | CK II inhibitor |
| Ochratoxin | stimulates ER $Ca^{2+}$ATPase |
| Ca-074-Me | Cathepsin B inhibitor |
| K252c | PKC inhibitor |
| Wortmannin | PI3 kinase, other kinases inhibitor |
| Actinomycin D | transcription inhibitor |
| AG213 | EGF-R inhibitor |
| BAPTA-AM | cell permeable $Ca^{2+}$chelator |
| Curcumin | Inductor of apoptosis in cancer cells |
| Puromycin | protein synthesis inhibitor |
| Bumetanide | $Na^+K^+Cl^-$cotransport inhibitor |
| Methyladenine [3-methyladenine] | autophagic inhibitor |
| H9 | kinase inhibitor |
| TPEN | cell permeable heavy metal chelator |
| spermine NONOate | NO donor |

In addition to the compounds above, 5,056 compounds from ICCB's commercial diversity set were screened, resulting in the identification of PD00600, 5323069, and 1M556S as potential positives. A number of the positives identified above, including alsterpaullone, H-9, curcumin, geldanamycin, AG370, Go6976, Spermine NONOate, PD00600, Nifedipine, α-amanitin, K252c, 5323069, 1M566S were further tested for their ability to inhibit monoubiquitination of the FANC D2 polypeptide, and/or render cisplatin hypersensitivity to 2008 cells expressing functional FANC F. The following examples describe the effects of three compounds, H-9, curcumin and alsterpaullone, in inhibiting the FA pathway.

Example 3

Figure 7:
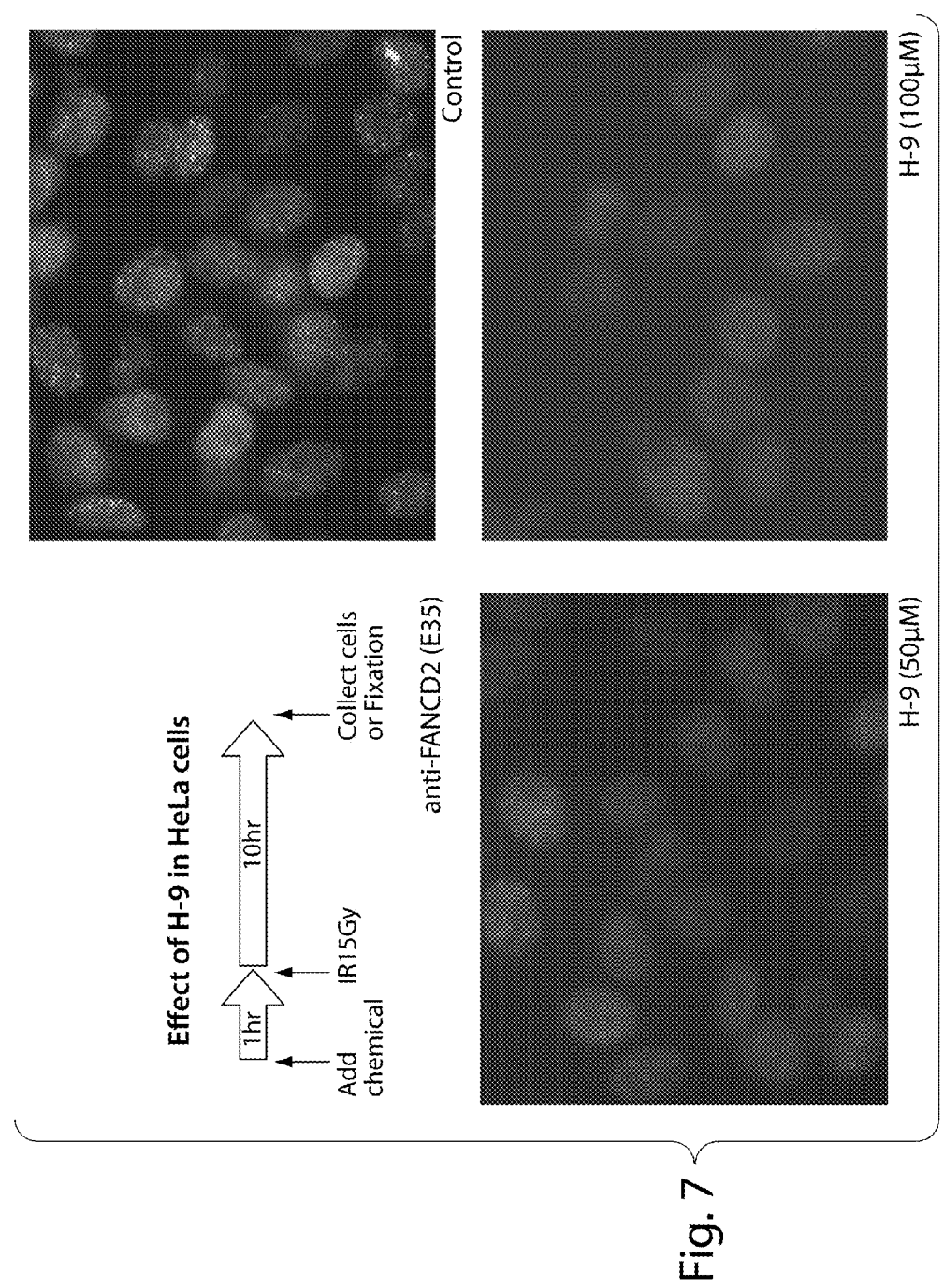
FIG. 7 are fluorescence micrographs showing inhibition of IR-mediated formation of FANC D2-containing foci upon exposure of eGFP-FANC D2 containing cells to the kinase inhibitor H-9.
Figure 9A:
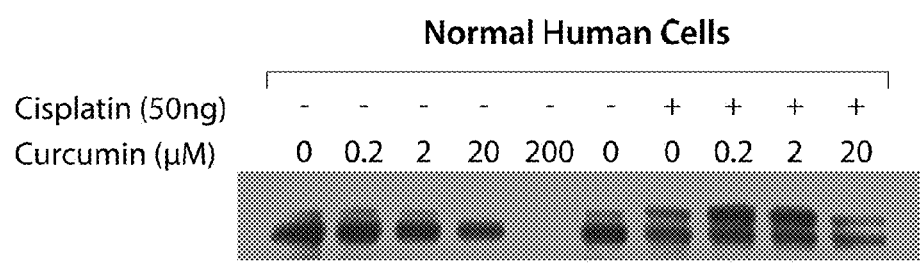
FIG. 9 shows the inhibition of cisplatin-dependent FANC D2 monoubiquitination by treatment with curcumin (9A). The graph (9B) shows the sensitization of FANCF-corrected 2008 cells to cisplatin, but a reduced sensitizing effect on the chemosensitization of the parental 2008 cells by curcumin treatment.
Figure 9B:
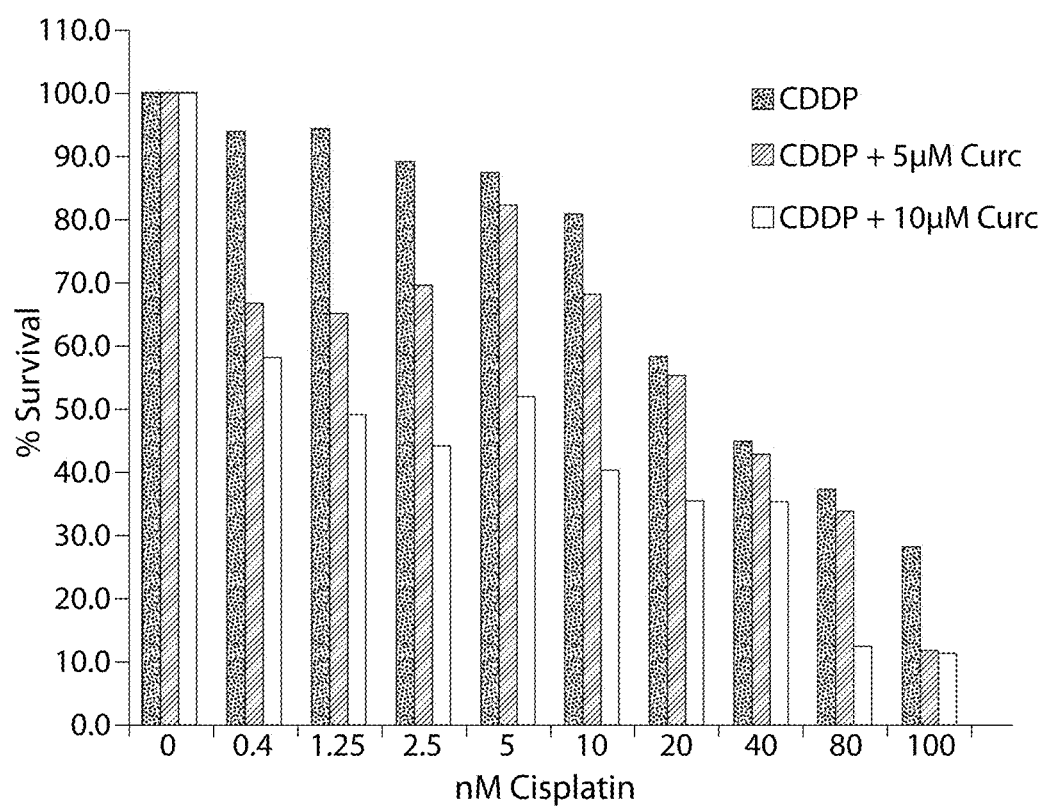

Identification and Characterization of H-9 as an Inhibitor of FANC D2 Ubiquitination and Foci Formation H-9 was identified as an inhibitor of the FA pathway using the high-throughput screen as described above. As shown by fluorescence microscopy in FIG. 7, H-9 inhibited the formation of FANC D2 foci in the 50-100 μM range. As a secondary screen using immunoblot analysis to determine the relative pools of monoubiquitinated FANC D2, H-9 treatment was found to decrease the overall level of FANC D2 monoubiquitination (FIG. 8). H-9 did not affect ATM-dependent phosphorylation of FANC D2 but did inhibit ATR dependent phosphorylation of CHK1. Finally, the hypersensitivity of the FANC F deficient 2008 cells, which is restored to wild-type levels when transfected with the FANCF cDNA, can be mimicked in 2008+FANCF cells by contacting the cells with curcumin (FIG. 9). Taken together, these results suggest that H-9 blocks the FA/BRCA pathway by inhibiting ATR kinase, either directly or indirectly.

Example 4

Figure 10:
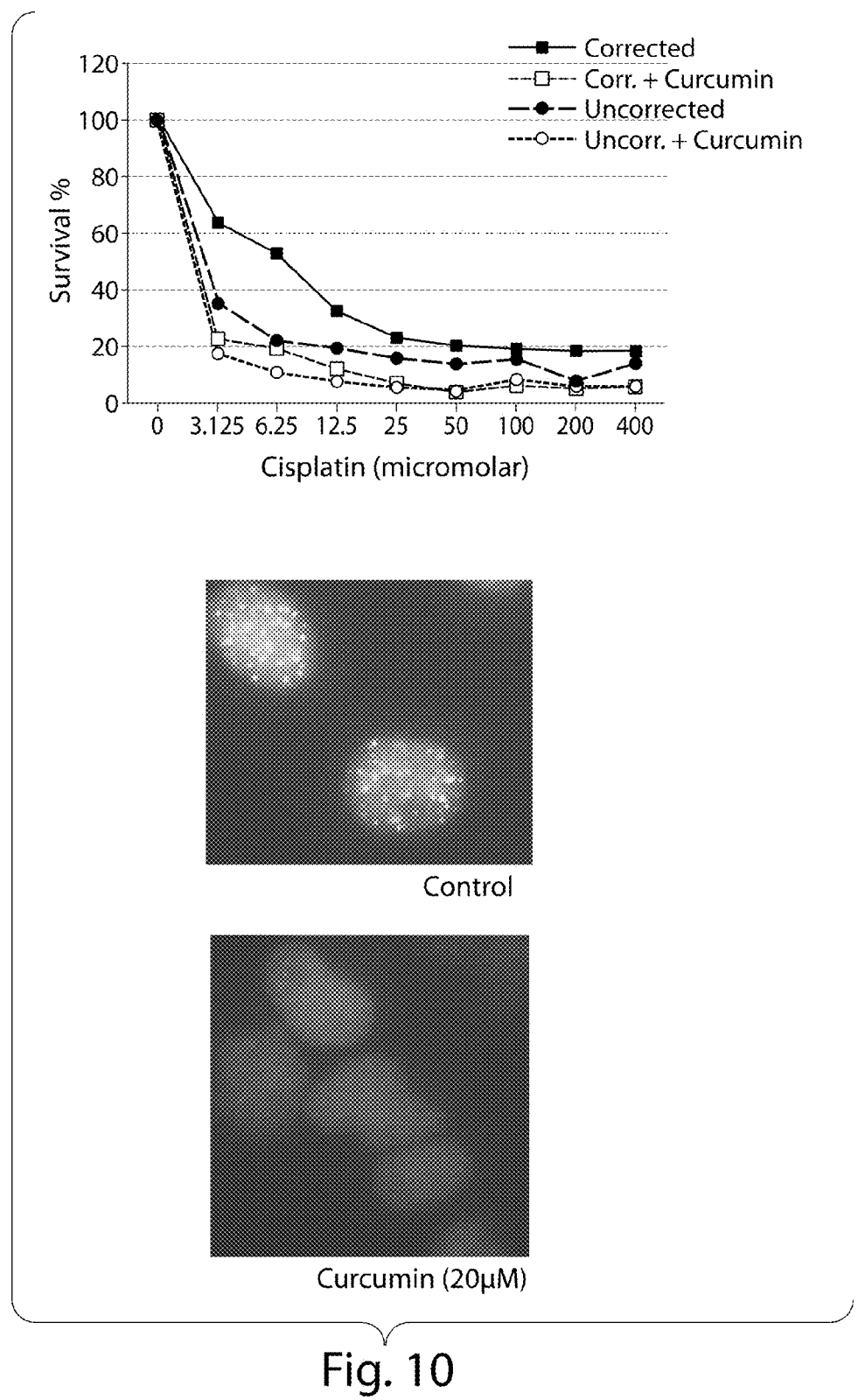
FIG. 10 shows the effects of curcumin on FANCD2 foci, and sensitivity towards cisplatin. (a) Curcumin sensitizes human tumor cells to Cisplatin. In this experiment we compared 2008 cells (an ovarian tumor line which is deficient in the FANCF protein and therefore has a defect in the FA pathway) and 2008 cells corrected with the FANCF cDNA. The cells were pretreated for 24 hours with or without curcumin (20 micromolar) as indicated, and the cells were then exposed to increasing doses of cisplatin. Importantly, the corrected 2008 cells are sensitized to cisplatin by pretreatment with curcumin. (b) Pretreatment of Clone 7 cells with Curcumin prevents the assembly of FANCD2 foci.
Figure 11:
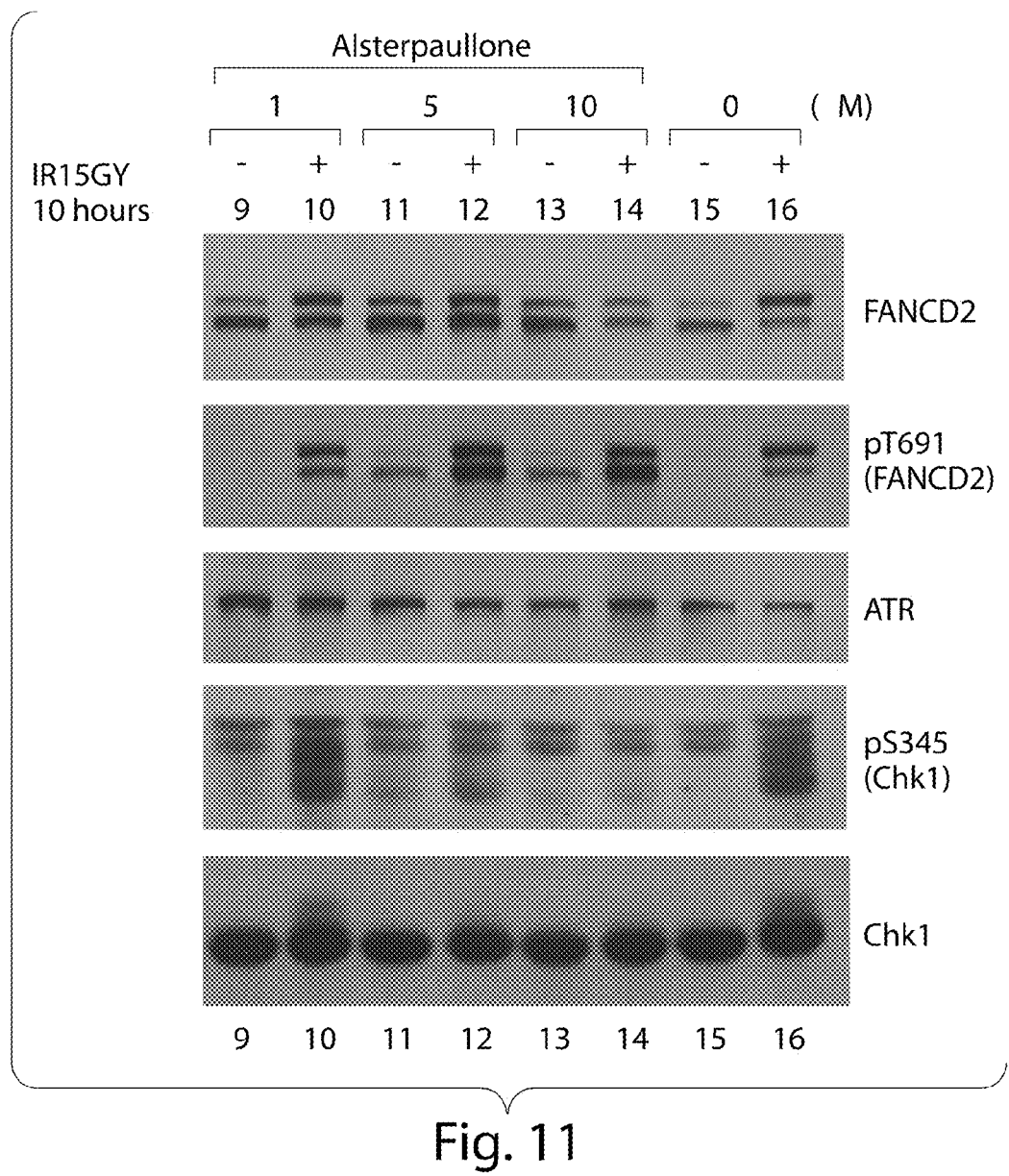
FIG. 11 shows an immunoblot analysis showing the effect of alsterpaullone on inhibition of IR-inducible monoubiquitination of FANC D2. Alsterpaullone, a Cdk1 inhibitor, does not inhibit IR-inducible D2 phosphorylation on T691 but rather enhances it. Alsterpaullone inhibits the IR-inducible monoubiquitination of FANC D2 and phosphorylation of Chk1 (on Ser345) in an ovarian cancer cell line.

Identification and Characterization of Alsterpaullone as an Inhibitor of FANC D2 Ubiquitination and Foci Formation Likewise, alsterpaullone was identified as a potential inhibitor of the FA pathway using the high-throughput screen. Alsterpaullone is known to inhibit Cdk1/cycline B, Gsk-3B, and Cdk5 (Sausville et al. (2000) *Ann N Y Acad. Sci.* 910:207-221; Schultz et al. (1999) *J Med. Chem.* 42:2909-2919). Alsterpaullone inhibited the formation of FANC D2 foci at a concentration of 10 μM (FIG. 10). Like H-9, alsterpaullone inhibited FANC D2 monoubiquitination and inhibited ATR dependent phosphorylation of Chk1 (FIG. 11).

Example 5

Identification and Characterization of Curcumin as an Inhibitor of FANC D2 Ubiquitination and Foci Formation The natural compound, curcumin, also caused a dose-dependent decrease in FANC D2 foci formation in the screening assay (data not shown). Furthermore, in the 3-20 micromolar range, curcumin caused a dose dependent decrease in FANC D2 monoubiquitination in HeLa cells and in cisplatin-exposed HeLa cells (FIG. 10). Curcumin also caused a dose-dependent decrease in ATR-mediated Chk1 phosphorylation (FIG. 11), further suggesting that curcumin blocks an upstream event in the FA/BRCA pathway.

Figure 12:
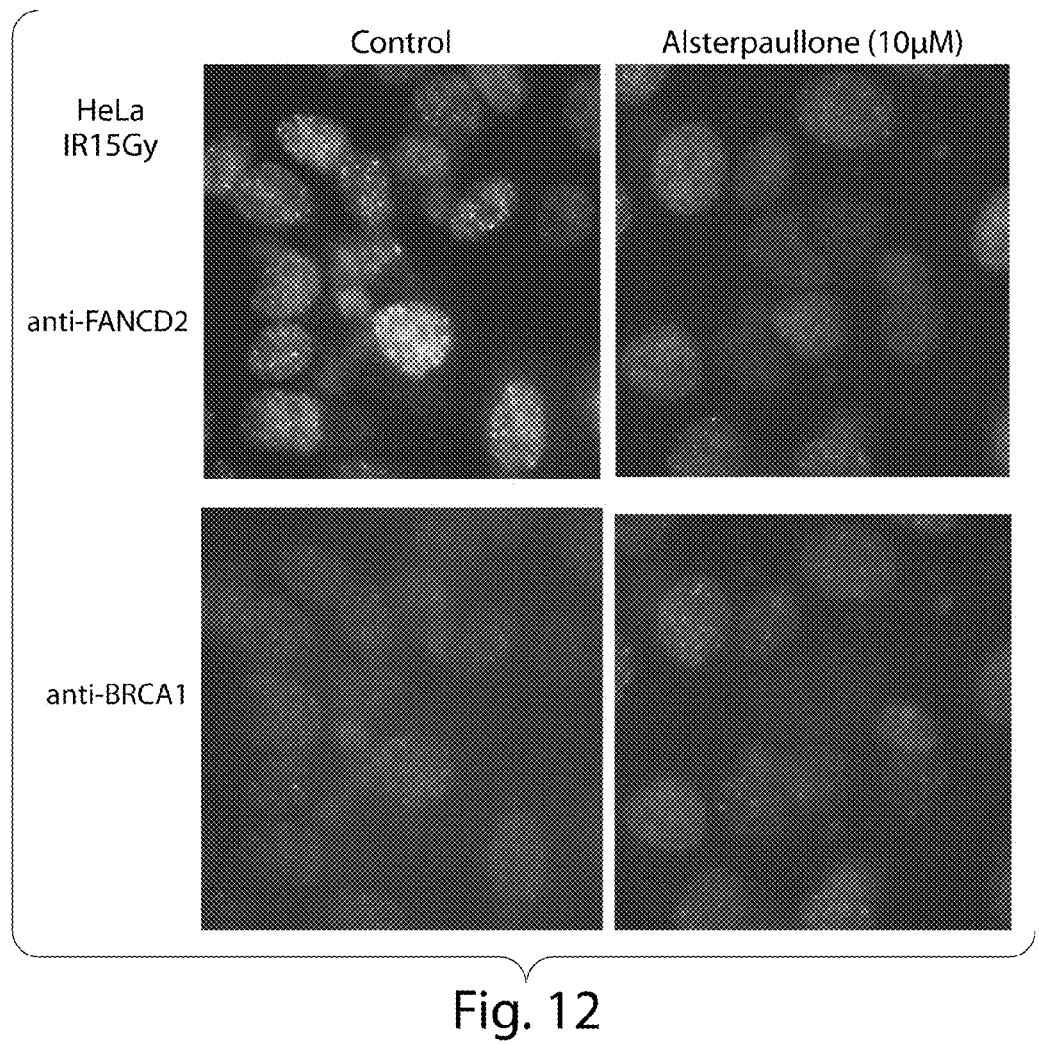
FIG. 12 are micrographs showing inhibition of IR-mediated FANC D2- and BRCA1-containing foci in cells treated with alsterpaullone.
Figure 13:
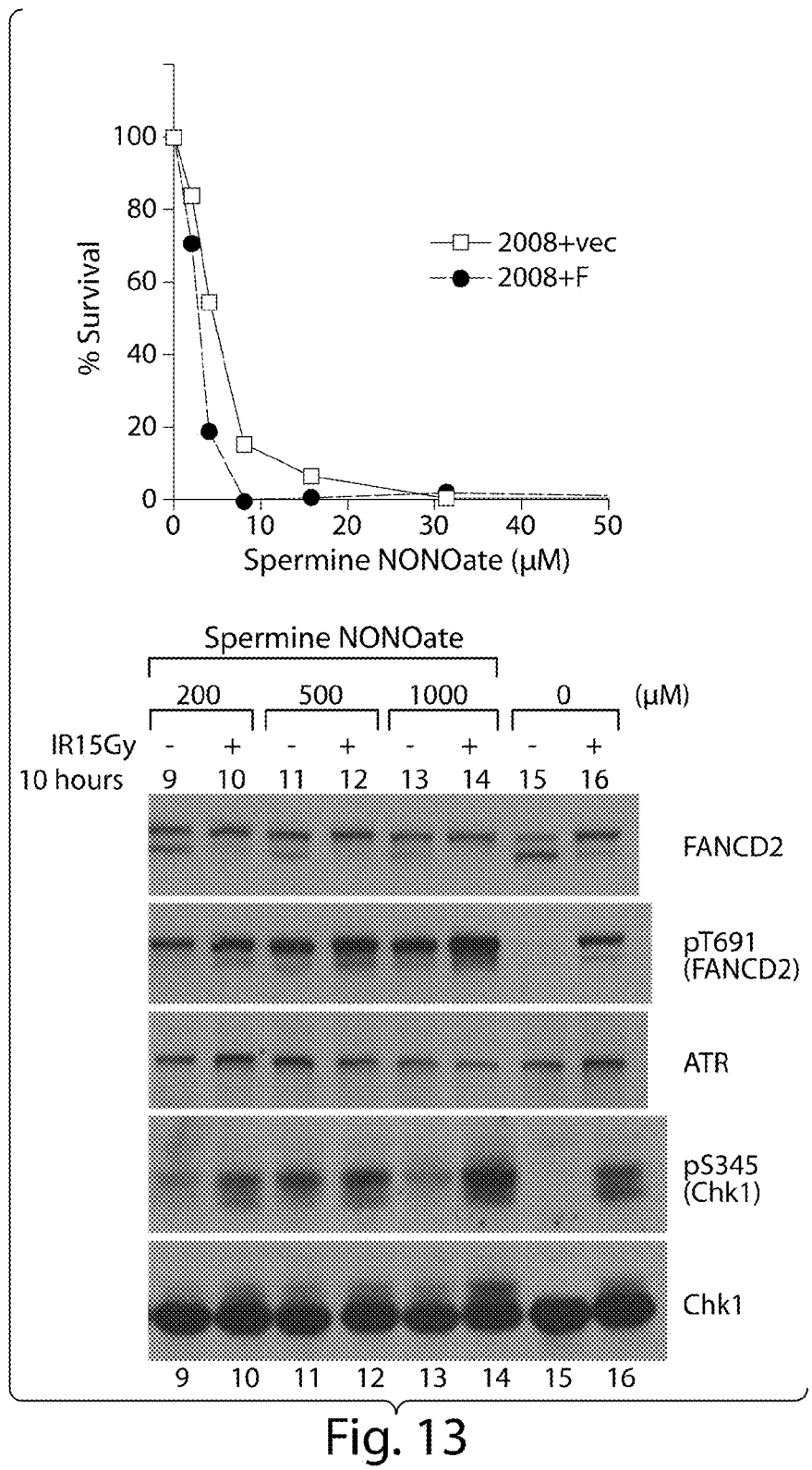
FIG. 13 shows that treatment of cells with spermine NONOate induces phosphorylation and monoubiquitination of FANC D2, and phosphorylation of Chk1 in the absence of IR. The graph shows a nominal reduction in sensitivity of 2008 cells to spermine NONOate upon FANC F transfection (2008+F), when compared with vector transfected 2008 cells (2008+vec).
Figure 14:
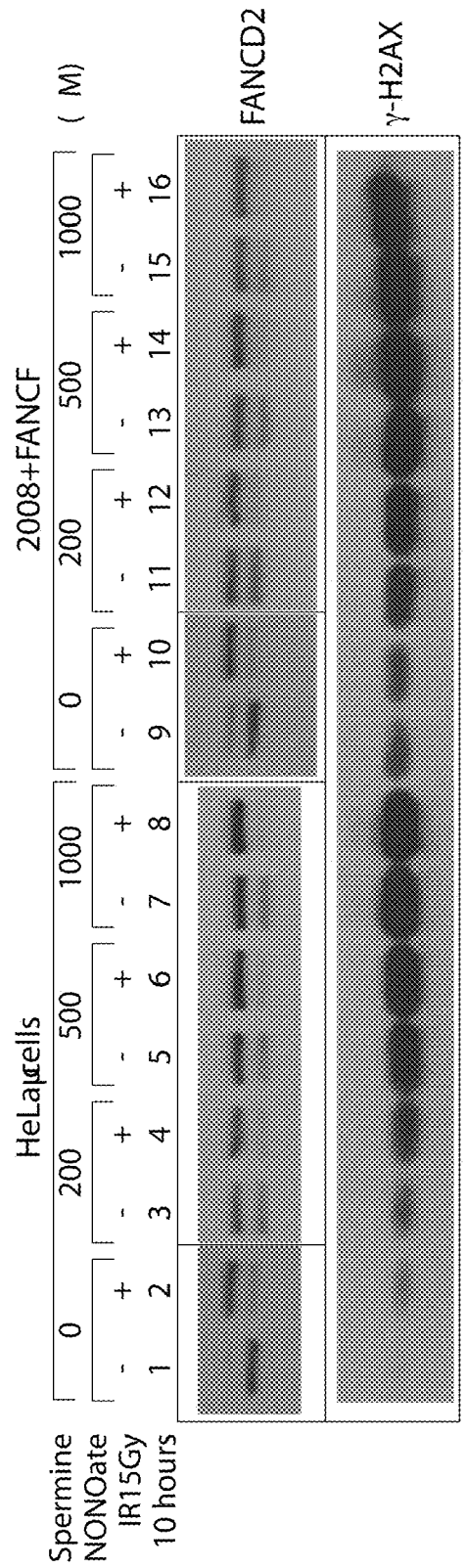
FIG. 14 shows that treatment of cells with spermine NONOate induces phosphorylation and monoubiquitination of FANC D2, and phosphorylation of Chk1 in the absence of IR.
Figure 15:
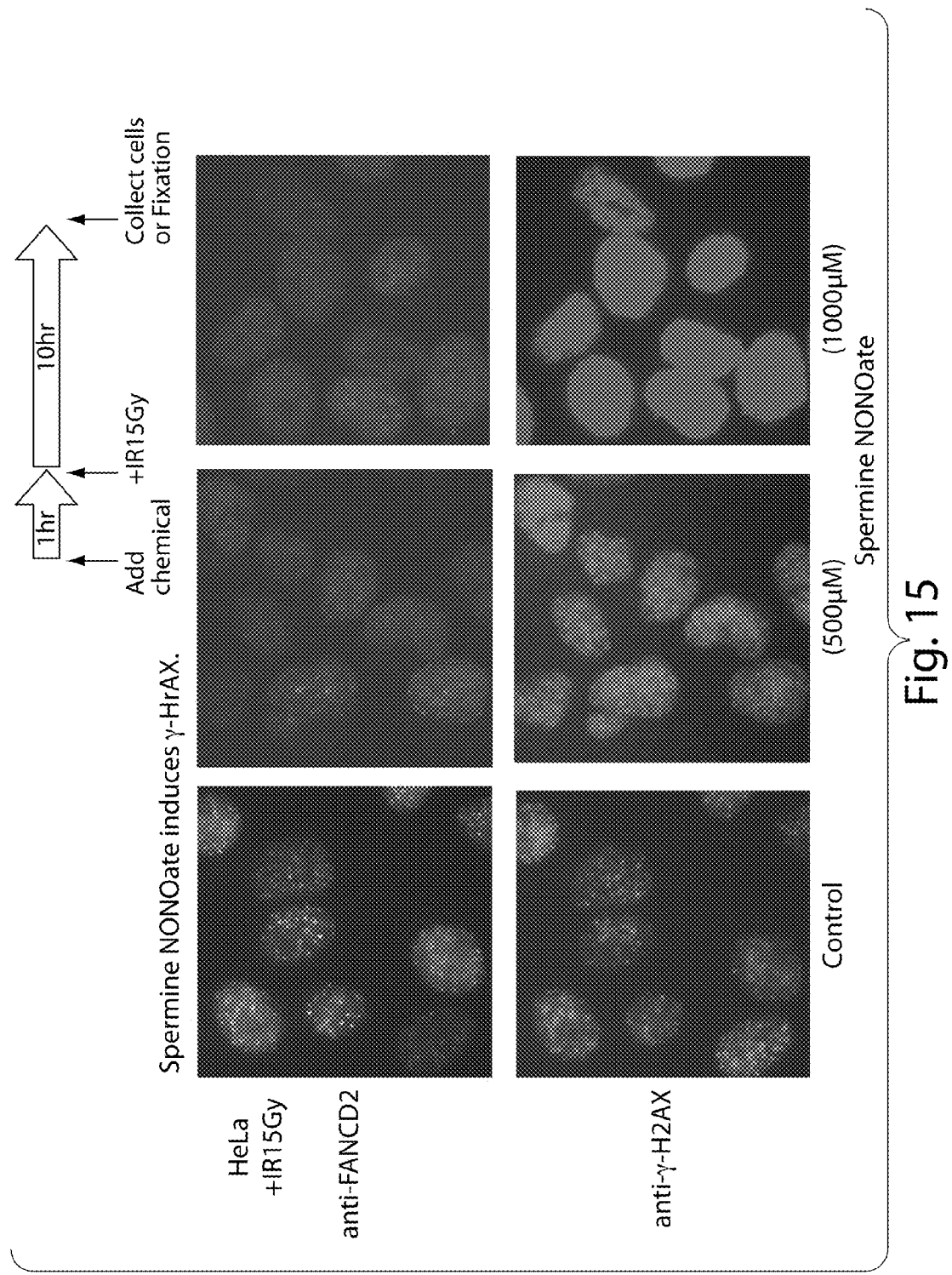
FIG. 15 are micrographs showing that spermine NONOate induces phosphorylation of histone H2AX in the absence and in the presence of IR treatment.
Figure 16:
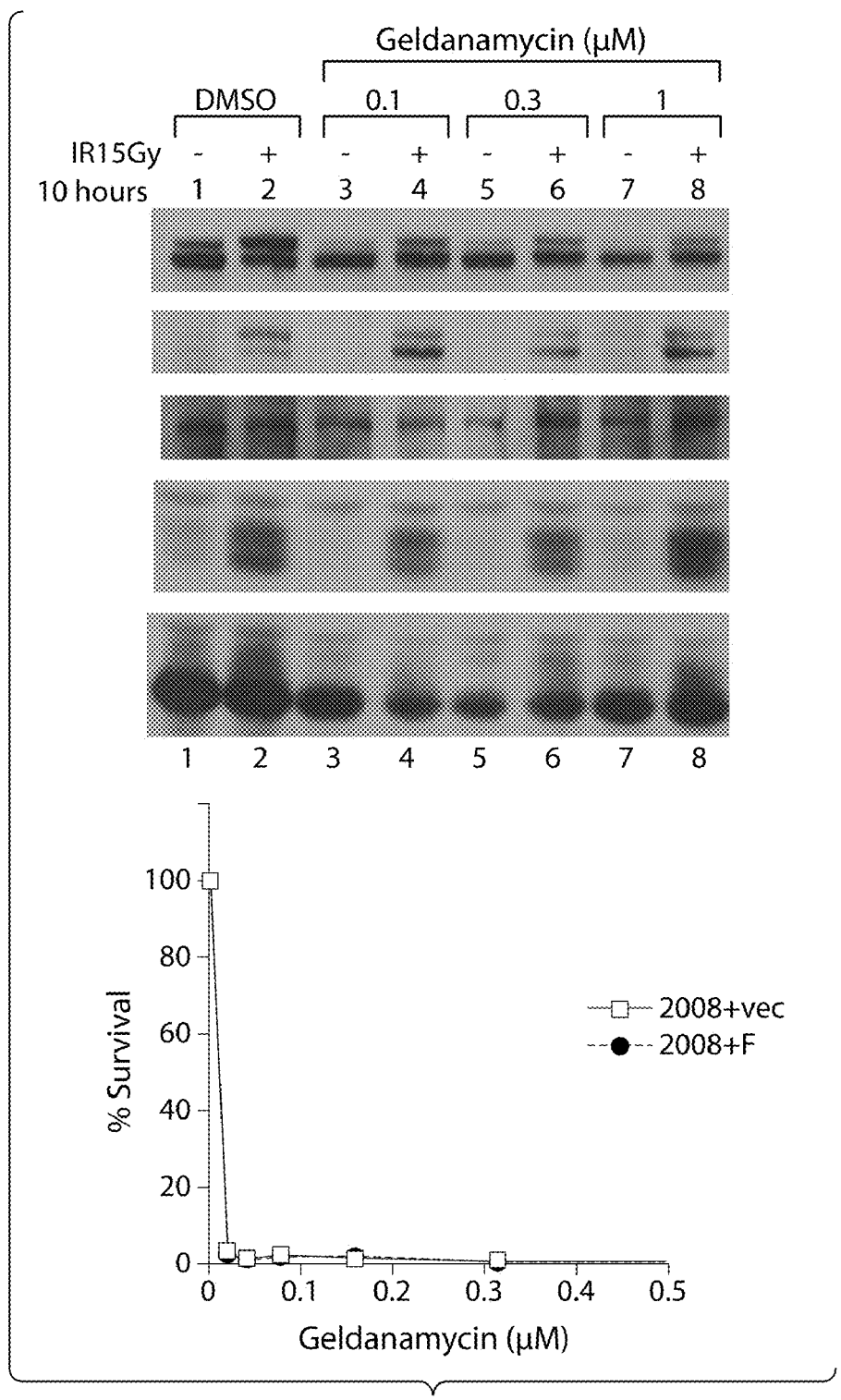
FIG. 16 shows an immunoblot analysis showing that geldanamycin (an Hsp90 inhibitor) inhibits IR-inducible D2 monoubiquitination in HeLa cells. Geldanamycin also causes decreased Chk1 expression. The graph shows that transfection of 2008 cells with FANC F does not alter sensitivity of cells to geldanamycin.
Figure 17:
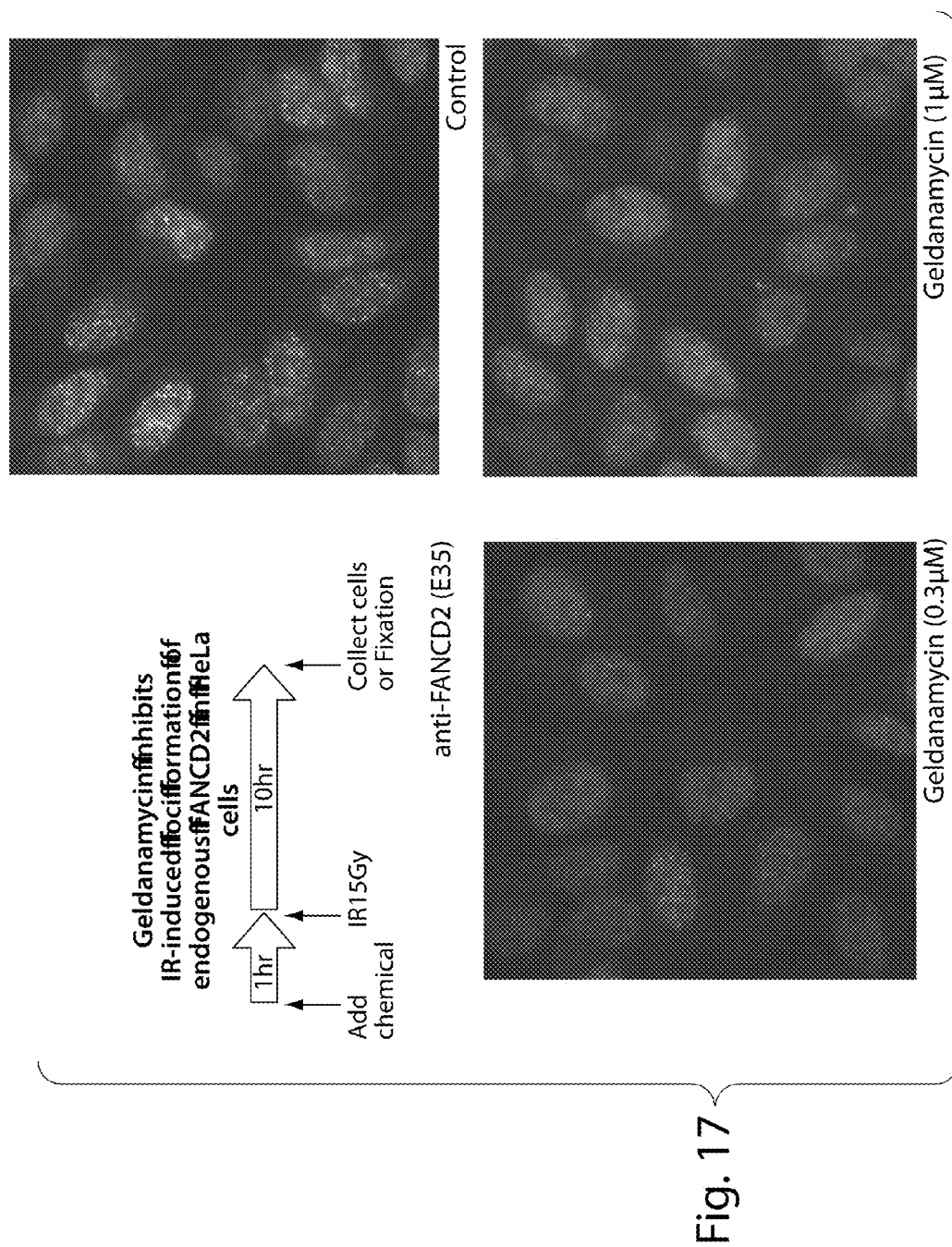
FIG. 17 are micrographs showing inhibition of IR-mediated FANC D2- and BRCA1-containing foci in cells treated with geldanamycin.
Figure 18:
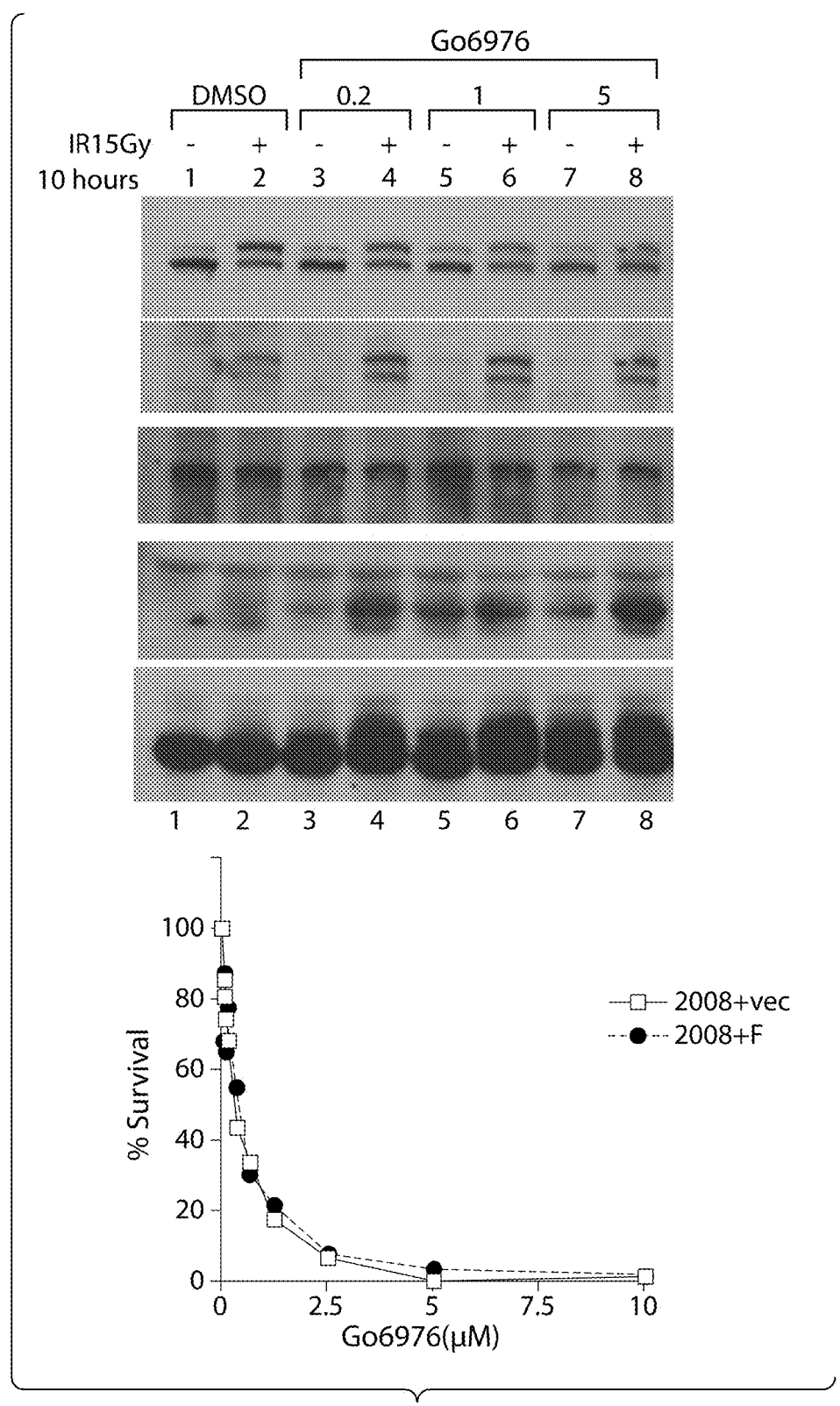
FIG. 18 shows the effects of Go6976, a PKC, Chk1 inhibitor, on IR-inducible monoubiquitination of FANC D2 in HeLa cells. Go6976 enhances phosphorylation of Chk1 in HeLa cells. However, transfection of 2008 cells with FANC F has no effect in sensitivity to Go6976.
Figure 19:
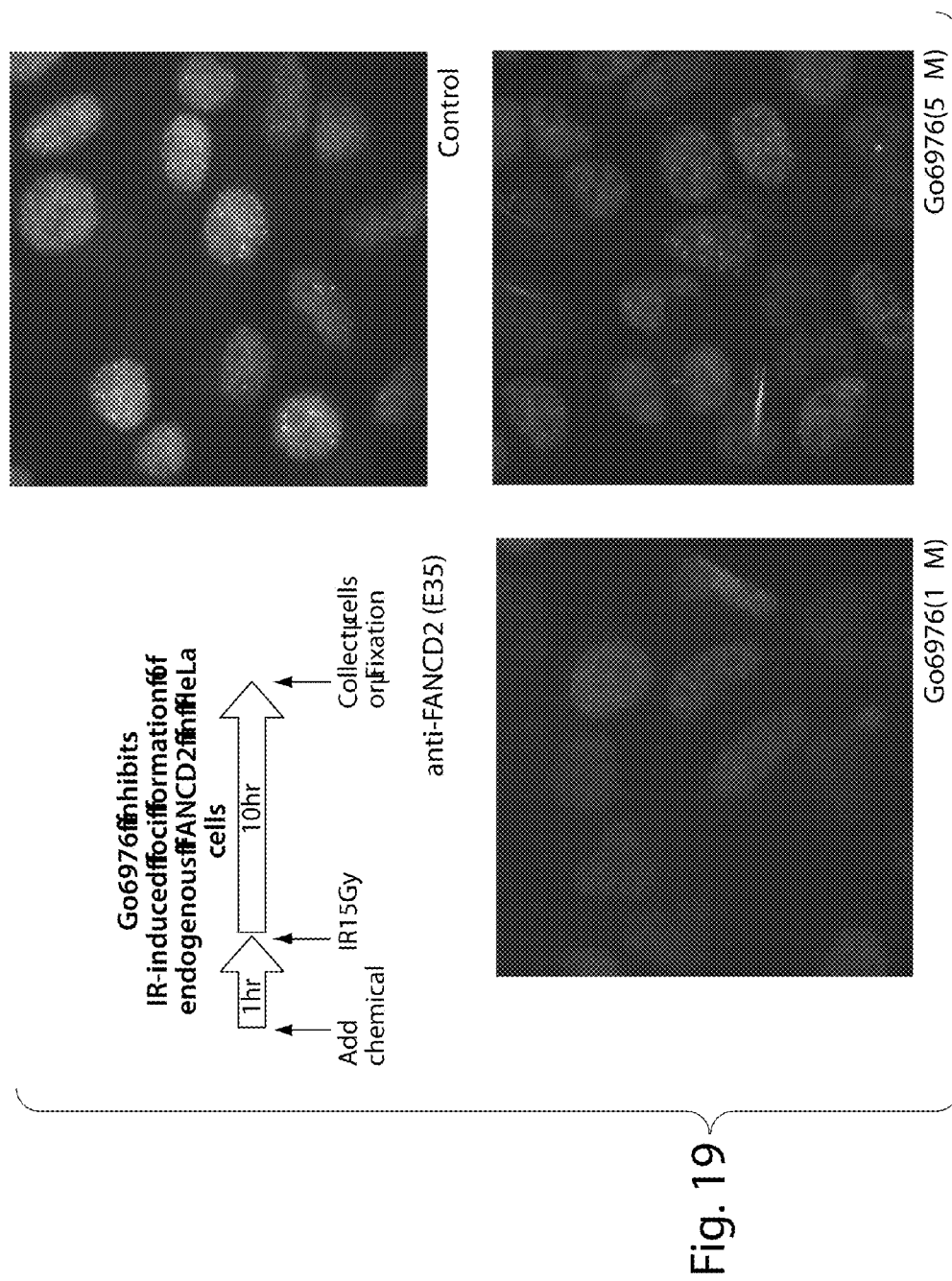
FIG. 19 are micrographs showing inhibition of IR-mediated FANC D2-containing foci formation in cells treated with Go6976.
Figure 20:
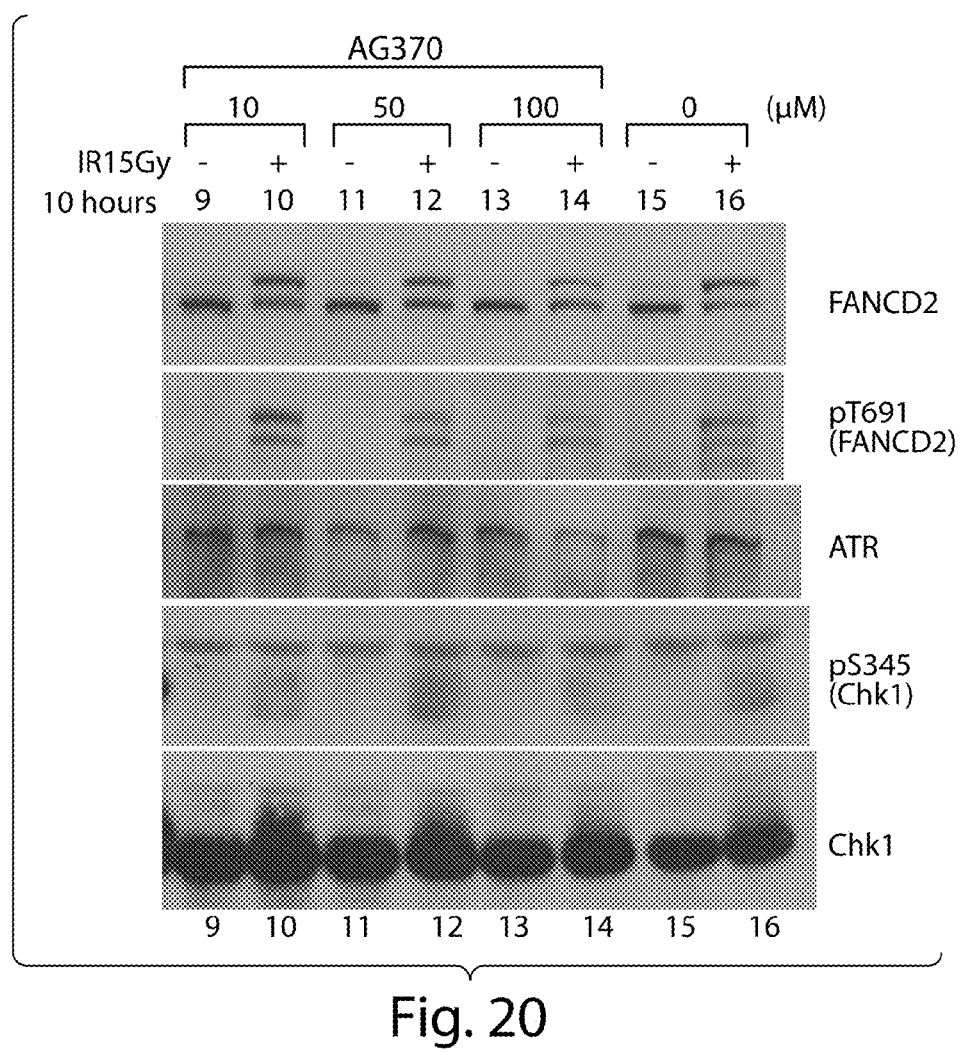
FIG. 20 are immunoblot panels showing the effects of AG370, a PDGFR kinase inhibitor, in inhibiting IR-inducible monoubiquitination of FANC D2 in HeLa cells. The effects of AG370 on Chk1 is not clear.
Figure 21:
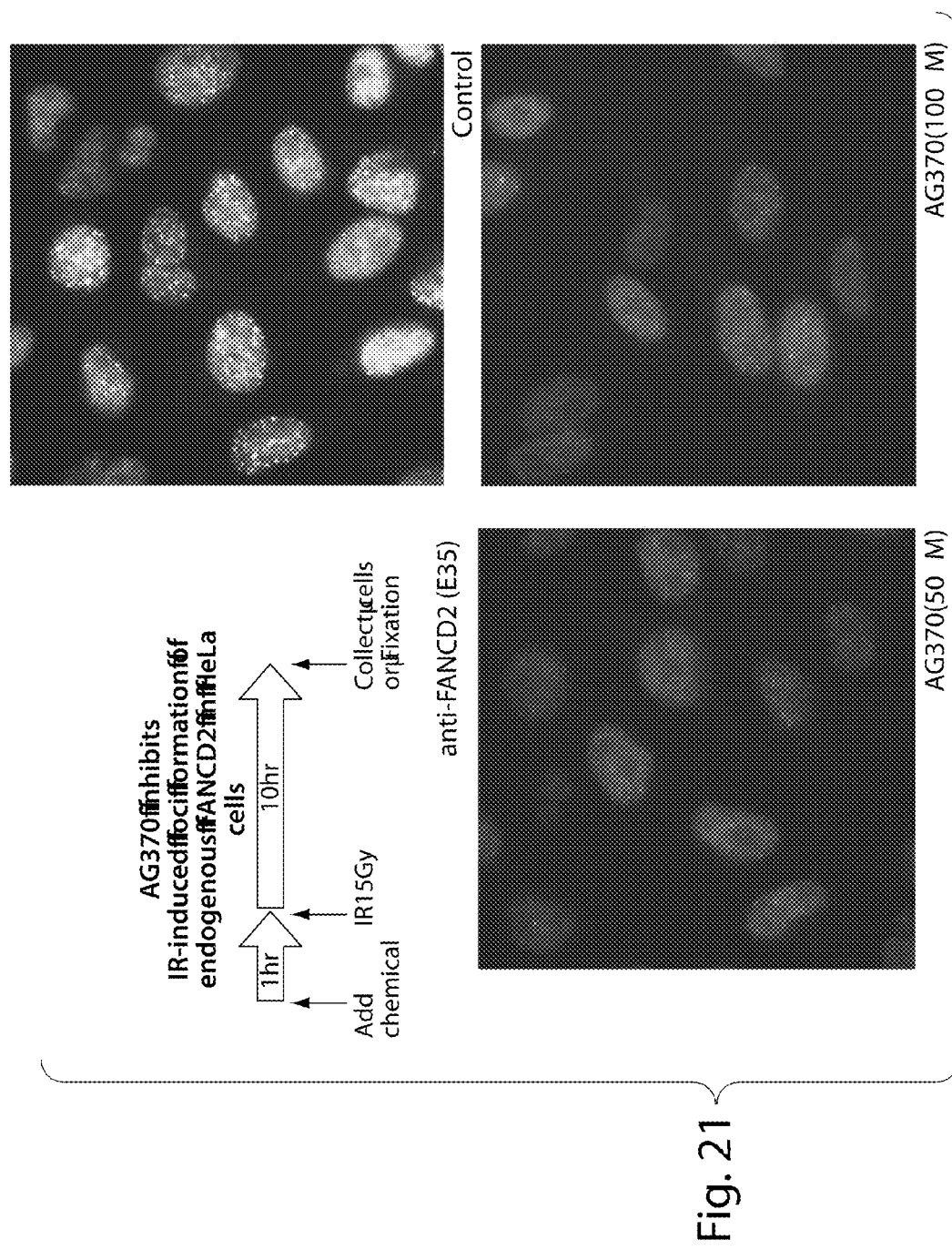
FIG. 21 are micrographs showing inhibition of IR-mediated FANC D2- and BRCA1-containing foci in cells treated with AG370.
Figure 22A:
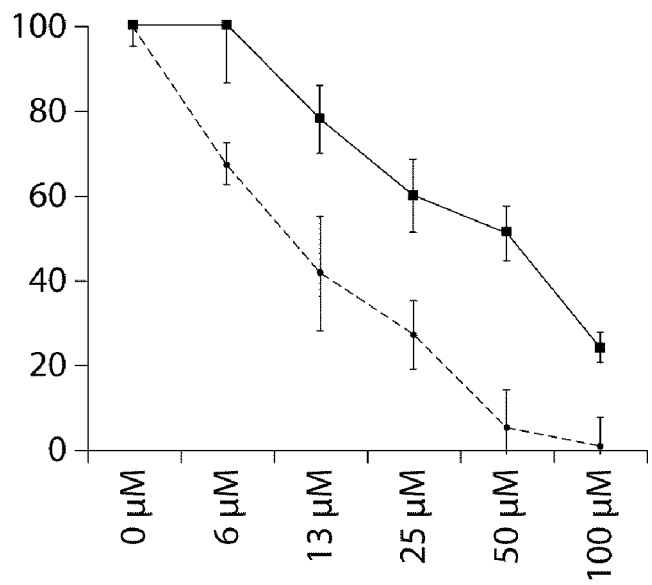
FIG. 22 shows that inactivation of the FA pathway causes increased sensitivity to DNA cross-linking agents, including BCNU. (a) Isogenic PD20 (circle) and PD20 retrovirally corrected with FANCD2 (square) showed differential sensitivity to BCNU. Percentage survival was plotted on the Y-axis. Similar data were obtained using 2008 (FANCF deficient cell line) and 2008 complemented with FANF. (b) Model of FA pathway. (c) BCNU induced FANCD2 monoubiquitination only in the presence of an intact FA pathway (lane 4). 2008 and 2008 retrovirally complemented with FANCF were either untreated or treated with BCNU. Whole cell lysates were fractionated on SDS-PAGE and immunoblotted with FANCD2 antisera. Similar data were derived using PD20 and PD20 corrected with FANCD2. (d) HT15 GBM cell lines failed to undergo FANCD2 monoubiquitination upon BCNU treatment. Other GBM lines tested (LN308, LN428, A172, T98G as shown above; CRL1620, CRL2020, U87, U343 (not shown)) underwent appropriate FANCD2 monoubiquitination on treatment with BCNU. (e) Failure to undergo FANCD2 monoubiquitination in HT15 cell lines correlated with increased sensitivity to BCNU. Percentage survival was plotted on the Y-axis.
Figure 22B:
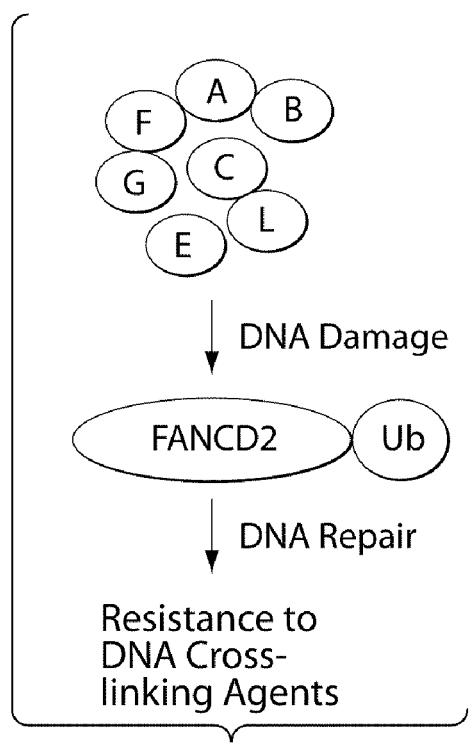
Figure 22C:
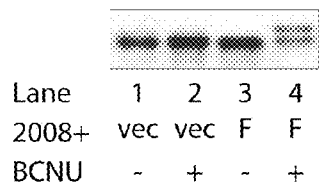
Figure 22D:
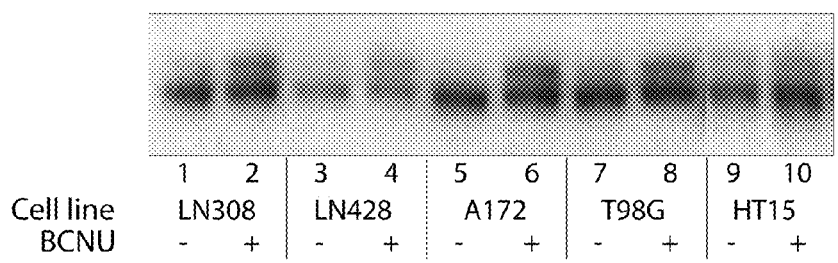
Figure 22E:
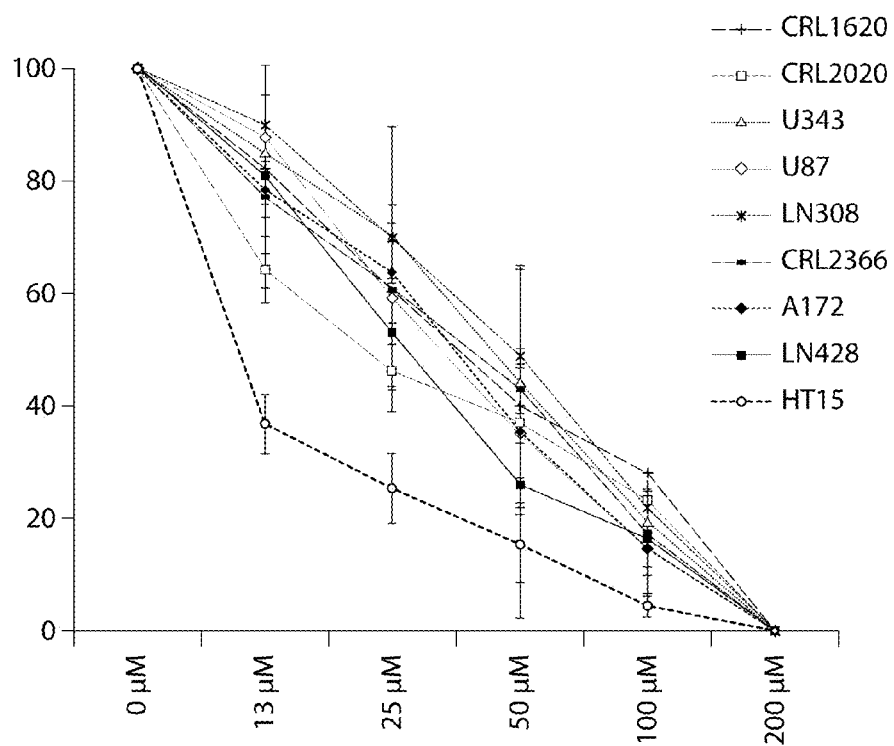

We next tested the ability of curcumin to potentiate the activity of cisplatin in cytotoxicity assays. Curcumin sensitized FANCF-corrected 2008 cells to cisplatin, but had a lesser effect on the chemosensitization of the parental 2008 cells (FIG. 12). Curcumin sensitized the cells in a dose range of 3-20 µM. This concentration range correlated with the curcumin dose range required for inhibition of the FA/BRCA pathway. Similar results were observed when the cells were pretreated for 24 hours with curcumin before the addition of cisplatin. Taken together, these results indicate that curcumin synergizes with cisplatin in enhancing ovarian tumor cytotoxicity and that this curcumin effect correlates with its inhibition of the FA/BRCA pathway.

Next, the synergistic effects of curcumin in breast cancer cell lines were assessed in order to see if the cytotoxic effects of cisplatin could be improved in cisplatin resistant cell lines. Thus, curcumin was tested for its effects in sensitizing a breast cancer cell line, MCF7 (ATCC) to cisplatin. These results were similar to those seen with the ovarian cancer cell lines. Both cisplatin and carboplatin demonstrated increased cytotoxicity with the addition of curcumin (5-20 µM). These doses also resulted in decreased FANC D2 monoubiquitination in this cell line, indicating inhibition of the FA/BRCA pathway (FIG. 12). Chk 1 phosphorylation was inhibited in all of the cell lines; 2008, 2008+F and MCF7 in a curcumin dose-dependent manner (FIG. 12).

The chemosensitizing activity of curcumin was further tested for its specificity to cisplatin. The ovarian tumor cell line, SKOV3, is sensitive to cisplatin and taxol (Yang and Page, (1995) *Oncol Res.* 7:619-24). Curcumin synergized with cisplatin in the killing of these cells. In contrast, curcumin had no effect on the dose dependent taxol cytotoxicity profile of these cells.

Example 6

Correction of Cisplatin Hypersensitivity in the Ovarian Cancer Cell Line 2008 by FANCF Complementation To determine whether these inhibitors are cisplatin-sensitizers two ovarian tumor lines—the cisplatin-sensitive, FANCF-deficient parental 2008 line and the 2008 line corrected with the FANCF cDNA. The parental 2008 line is deficient in FANCF due to epigenetic silencing of the FANCF gene (Taniguchi et al., (2003) *Nat Rev Cancer.* 3:23-34). Alsterpaullone enhanced the cytotoxicity of cisplatin in the FANCF cDNA corrected cells, but not in the parental 2008 cells, indicating that this kinase inhibitor is a potential cisplatin sensitizer and that it works through inhibition of the FA pathway (FIG. 11). Curcumin sensitized FANCF-corrected 2008 cells to cisplatin, but had a lesser effect on the chemosensitization of the parental 2008 cells (FIG. 9, and Table 3). Curcumin sensitized the cells in a dose range of 3-20 micromolar, corresponding to the curcumin dose range required for inhibition of the FA/BRCA pathway. Similar results were observed when the cells were pretreated for 24 hours with curcumin before the addition of cisplatin (data not shown). Taken together, these results indicate that curcumin synergizes with cisplatin in enhancing ovarian tumor cytotoxicity and that this curcumin effect correlates with its inhibition of the FA/BRCA pathway.

Example 7

Determination of the Maximum Tolerated Dose for Intraventricular Administration of FA Pathway Inhibitors FA pathway inhibitors Curcumin and Alsterpaullone are soluble at up to 2.5 mM in 25% DMSO, the maximum concentration compatible with intraventricular administration. Taking into consideration that the entire mouse ventricular system consists of no more than 20 µl, the maximum concentration achieved (50 µM) exceeds that required for FA pathway inhibition. Likewise, both AMD3100 and O6 Benzylguanine are sufficiently soluble in media, allowing estimated intraventricular concentrations to exceed those required for efficacy in vitro. For each compound tested, a group of six mice are implanted with intraventricular catheters (4 mm anterior to the lambda suture, 0.7 mm lateral of midline, and 2.5 mm below the dura). The catheters are connected to a subcutaneous Alzet Osmotic pump model 1007D (90 µl volume delivered at 0.5 µl/hr) containing 2.5 mM, 1.25 mM, 0.625 mM, 0.313 mM, 0.151 mM of each compound or the vehicle media. The mice are monitored daily during the infusion period for neurologic deficits and sacrificed at postoperative day 21. Brain sections are performed to 1) confirm catheter continuity with the lateral ventricle, and 2) assess cellular toxicity by stained with hematoxylin and eosin as well as TUNEL staining. The highest dose of drug delivered without clinical or histologic evidence of damage are selected for subsequent efficacy studies, as detailed below.

Example 8

In vivo Tumoricidal Effects of Systemic BCNU Administration by Intravesicular Administration of an FA Pathway Inhibitor The mouse xenograft, bioluminescence model used herein employs the U87 GMB cell line (ATCC), which has been retrovirally transfected with the coding sequence for luciferase in a pMMP vector. Established U87-Luciferase cell lines are harvested in mid-logarithmic growth phase, resuspended as 50,000 cells in 10 µl PBS, and introduced into mice brain using stereotactic guidance (2 mm lateral and posterior to the bregma, 3 mm below dura). Mice are given D-luciferin (Xenogen, Alameda, Calif.) intraperitoneal injections and imaged with the IVIS imaging system (Xenogen) on post-surgery day 5 and 10.

For each compound tested, a group of 30 mice are implanted with U87-Luciferase and surveyed on post-implant day 5 and 10, out of which 20-26 mice are expected to have uptake of the implanted tumor (Rubin et al., (2003) *Proc. Natl. Acad. Sci. USA,* 100: 13513-13518). Mice with U87-

Luciferase tumor uptake are then surgically implanted with an intraventricular catheter and Alzet pump 1007D. These mice are then stratified into four groups:
- Group 1: treated with control vehicle (25% DMSO)
- Group 2: treated with i.p. BCNU administration (15 mg/kg);
- Group 3: treated with i.p. administration of an FA inhibitor at the maximum tolerated dose; and
- Group 4: treated with i.p. BCNU administration (15 mg/kg) as well as FA inhibitor at the maximum tolerated dose.

The intraventricular catheter is placed contra-lateral to the tumor implant site to minimize the effect of tumor growth on stereotactic coordinates. The i.p. BCNU injection is carried out 4 days after intraventricular administration to allow for sensitization. The mice are imaged on day 15 and 20 after initial tumor implant. Comparison of tumor growth is determined using LIVING IMAGE software package (Xenogen).

Example 9

Efficacy of FA Inhibitor in Sensitizing Ovarian Tumors to Anti-neoplastic Agents in an Animal Model A number of animal models for ovarian cancer are known in the art. For example, Connolly et al. ((2003) *Cancer Research,* 63, 1389-1397), which is incorporated herein by reference, discloses methods of developing epithelial ovarian cancer in mice by chimeric expression of the SV40 Tag under control of the MISIIR promoter. In another example (Liu et al., (2004) *Cancer Research* 64, 1655-1663), which is also incorporated herein by reference, disclose the introduction of human HRAS or KRAS oncogenes into immortalized human ovarian surface epithelial cells, which form s.c. tumors after injection into immunocompromised mice. These mice models provide useful means to test the efficacy of FA inhibitors in sensitizing ovarian tumors to anti-neoplastic agents. 6 mice are used per group. To test the efficacy of cisplatin, alone or in combination with the FA inhibitor alsterpaullone, the following groups were used:
- Group 1: treated with control vehicle
- Group 2: treated with cisplatin, 4 mg/kg;
- Group 3: treated with alsterpaullone at 5 mg/kg
- Group 4: treated with cisplatin, 4 mg/kg, and alsterpaullone, 5 mg/kg. Repeat the cycle after two days.

All treatments are started a week after tumor inoculation. Mice are treated for 10 cycles in total, and sacrificed for tumor nodule counting two weeks (on day 50) after discontinuation of drug treatment. Upon sacrifice, antitumor activity in each group is evaluated by counting the number of tumor nodules in the peritoneal cavity, measuring the diameter of the tumors, measuring the volume of the ascites and qualitatively observing the color of the peritoneal wall as an indication of the degree of tumor-induced vascularization. Toxicity is evaluated by qualitative observation of the general appearance and behavior of the mice prior to sacrifice and by measuring their body weight at various intervals during the course of the treatments.

It will be clear to those skilled in the art that the efficacy of other FA inhibitors, such as curcumin, alsterpaullone and H-9, can be tested using this procedure. Curcumin is known to be safe at high doses, with $LD_{50}$ of greater than 10,000 mg/kg. Curcumin can be administered orally, intraperitoneally or intravesicularly. In one example, i.p. administration of curcumin at 100 mg/kg-300 mg/kg is performed, either alone or in combination with an anti-neoplastic agent (e.g., cisplatin) is tested in mice, as described above. In another example, intravesicular administration of curcumin is performed at the highest possible dose determined using the method outlined above.

Example 10

Efficacy of a Combination of an FA Inhibitor and a DNA Damage Repair Pathway Inhibitor in Treating Ovarian Tumor The efficacy of a combination of an FA inhibitor and an inhibitor of a DNA damage repair pathway is tested essentially as described above in Example 6. Briefly, the efficacy of the FA inhibitor (for example, curcumin, H-9, or alsterpaullone) in treating ovarian tumor, is tested alone or in combination with a DNA damage repair pathway inhibitor. In one example, the following groups are tested:
- Group 1: treated with control vehicle
- Group 2: treated with alsterpaullone at 5 mg/kg
- Group 3: treated with methoxyamine at 2 mg/kg
- Group 4: treated with alsterpaullone, 5 mg/kg, and methoxyamine, 2 mg/kg. Repeat the cycle after two days.

Progress is monitored as previously described.

Example 11

Combination of an FA Inhibitor and a DNA Damage Repair Pathway Inhibitor in Sensitizing Ovarian Tumors to Anti-Neoplastic Agents In this example, the ability of a combination of an FA pathway inhibitor such as curcumin, H-9 or alsterpaullone, and a DNA damage repair pathway inhibitor such as methoxyamine, in sensitizing a tumor to anti-neoplastic agents is tested using an animal model, essentially as described above. However, the dosage of anti-neoplastic agent administered can be varied to determine whether sensitization results in a lower overall dosage of the antineoplastic agent necessary to treat the tumor. The following groups of mice are tested:
- Group 1: treated with control vehicle
- Group 2: treated with cisplatin, 0 mg/kg; alsterpaullone, 5 mg/kg, and methoxyamine, 2 mg/kg
- Group 3: treated with cisplatin, 1 mg/kg; alsterpaullone, 5 mg/kg, and methoxyamine, 2 mg/kg
- Group 4: treated with cisplatin, 2 mg/kg; alsterpaullone, 5 mg/kg, and methoxyamine, 2 mg/kg
- Group 5: treated with cisplatin, 4 mg/kg; alsterpaullone, 5 mg/kg, and methoxyamine, 2 mg/kg Progress is monitored as previously described.

TABLE 3

Chemosensitization of the Ovarian tumor line, 2008 + FANCF to Cisplatin.

| Inhibitor | 2008 | 2008 + FANCF |
|---|---|---|
| Solvent (DMSO) | S | R |
| Wortmannin | S | S |
| H-9 | S | S |
| Alsterpaullone | S | S |
| Curcumin | S | S |

S, Hypersensitive to Cisplatin;
R, Resistant to Cisplatin

Example 12

Clinical Evaluation of Treatment of Recurrent Mullerian Malignancies With Curcumin and Carboplatin A Phase I open-label, dose-escalation safety study is conducted in patients with recurrent carcinoma of mullerian origin, less than 12 months from prior platinum-based chemotherapy. Curcumin is administered orally the night before, immediately prior to, the night of, and the morning following intravenous administration of carboplatin AUC 5. A treatment cycle is 28 days with carboplatin adminstration beginning on day 1 followed by a 28-day follow-up period. Decisions regarding dose escalation and Dose Limiting Toxicity determination are made at the end of the 4 week cycle. Patients who tolerate treatment without evidence of disease progression are eligible for additional cycles of curcumin/carboplatin treatment.

Initially three patients will be entered in the first dose level. The initial dose level will be carboplatinum AUC 5 and curcumin 900 mg. If none has Dose Limiting Toxicity (DLT), then the next 3 patients get dose level 2. If a DLT occurs at any dose level, three additional patients are enrolled to that dose level. If two DTLs occur at that dose level, then it is declared above the Maximum Tolerated Dose (MTD) and the MTD is defined at the previous dose level. No intrapatient dose escalations are made.

Study Agent Administration

The initial dose will be carboplatin AUC 5 infused over 60 minutes and curcumin 900 mg taken orally. During the study period, only the curcumin dose will be escalated while the carboplatin dose will remain constant based on the patient's renal function. A cycle is defined as an interval of 28 days and is comprised of one treatment of carboplatin on Day 1 of the cycle and one course of curcumin administered the day prior (Day0), immediately prior to carboplatin on Day 1, the night of Day 1, and the morning of Day 2 for a total of 4 doses during each cycle. The doses of curcumin will be escalated for additional cohorts of patients until the DLT and MTD are determined.

Dose Escalation Schedule

| Dose Level | Carboplatin | Curcumin |
|---|---|---|
| 1 | AUC 5 | 900 mg |
| 2 | AUC 5 | 1800 mg |
| 3 | AUC 5 | 2700 mg |
| 4 | AUC 5 | 3600 mg |
| 5 | AUC 5 | 4500 mg |

Carboplatin Administration

Carboplatin is infused intravenously over 1-hour. The dose of carboplatin is calculated as follows, using the Calvert formula based on creatinine clearance:

Total dose (mg)=Target $AUC$ (in mg/ml per min)×(Estimated $GFR$+25)

The carboplatin dose is calculated in mg, not mg/m². The initial target AUC for carboplatin treatment in this trial is AUC=5. Creatinine clearance (CRCL) can either be measured, or estimated using the Jelliffe formula. Jelliffe formula For females:

$$GFR = \frac{0.9 \times (98 - 0.8(age^* - 20))}{Cr(mg/dl)}$$

* Age rounded to the nearest decade

Individual preferences for carboplatin antiemetic pre-medication are permitted. Typical pre-mediations include, zofran, ativan and decadron.

Definition of Dose-Limiting Toxicity (DLT)

The determination of DLT for purposes of assessing dose escalation is defined as follows using the NCI CTC version 3.0 criteria with consideration of known and accepted toxicities of carboplatin. Toxicities reached without pre-medication are not considered DLT.

Any nausea, vomiting >Grade 3 with maximum antiemetic pre-medication.

All other drug-related non-hematologic toxicity >Grade 3

Hematologic Toxicity

Neutrophil count <500 cell/ul for >7 days

Any febrile neutropenia (defined as T>101° F.) with a neutrophil count <500 cells/ul after curcumin/carboplatin administration Platelet count <10,000 cell/ul OR Grade 3 with evidence of bleeding necessitating blood product or platelet transfusion.

Hemoglobin >Grade 4 toxicity with erythropoietin co-administration

Evaluation of Response

Patients with measurable disease will be assessed by standard criteria. Patients are reevaluated after every two cycles of carboplatin/curcumin. In addition to a baseline/screening scan, confirmatory scans are obtained 4 weeks following initial documentation of an objective response.

Definitions

Response and progression are evaluated in this study using the new international criteria proposed by the Response Evaluation Criteria in Solid Tumors (RECIST) Committee (JNCI 92(3):205-216, 2000). Changes in the largest diameter of the tumor lesions are used in the RECIST criteria. Lesions are either measurable or nonmeasurable using the criteria listed below.

Guidelines for Evaluation of Measurable Disease:

At baseline, tumors lesions are categorized as follows:

(1) measurable—lesions that can be accurately measured in at least one dimension as 20 mm with conventional techniques or as 10 mm with spiral CT. OR (2) nonmeasurable—all other lesions All measurements are recorded in metric notation. All baseline evaluations are performed as closely as possible to the beginning of treatment and never more than 4 weeks before the beginning of treatment. Non-measurable disease includes the following: bone lesions, leptomeningeal disease, ascites, pleural/pericardial effusion, abdominal masses that are not confirmed and followed by imaging techniques, and cystic lesions.

Specifications by Methods of Measurements

The same method of assessment and the same technique is used to characterize each identified and reported lesion at baseline and during follow-up. Imaging-based evaluation is preferred to evaluation by clinical examination when both methods have been used to assess the antitumor effect of treatment.

Clinical Examination

Clinically detected lesions are considered measurable when they are superficial (i.e. skin nodules and palpable lymph nodes). All skin lesions are documented with color photography, including a ruler to estimate the size of the lesion.

Chest X-Ray

Although lesions on chest x-ray are acceptable as measurable lesions when they are clearly defined, a CT is preferable.

Computed Tomography (CT) and Magnetic Resonance Imaging (MRI)

CT and MRI are the best available (and most reproducible) methods for measuring target lesions selected for response assessment. Conventional CT and MRI are performed with contiguous cuts of 10 mm or less in slice thickness.

Ultrasound

Ultrasound is not used to measure tumor lesions. Ultrasound can be considered a possible alternative to clinical measurements for superficial palpable lymph nodes and subcutaneous lesions.

Tumor Markers

Tumor markers alone are not used to assess response. However, if markers are initially above the upper limit, they must return to normal levels for a patient to be considered in complete clinical response when all tumor lesions have disappeared.

Cytology, Histology

These techniques are used to differentiate between partial responses (PR) and complete responses (CR) in rare cases where residual lesions in tumor types can contain benign components.

The cytological confirmation of the neoplastic origin of any effusion that appears or worsens during treatment when the measurable tumor has met criteria for response or stable disease is mandatory to differentiate between response or stable disease and progressive disease.

Tumor Response Evaluation

Documentation of "Target" and "Nontarget" Lesions

All measurable lesions up to a maximum of 5 lesions per organ and 10 lesions in total, representative of all involved organs, are identified as target lesions and recorded and measured at baseline. Target lesions are selected on the basis of their size (those with the longest diameter) and their suitability for accurate repeated measurements (either by imaging techniques or clinically). A sum of the longest diameter for all target lesions is calculated and reported as the baseline sum longest diameter. The baseline sum of the longest diameter is used as the reference by which to characterize the objective tumor response.

All other lesions (or sites of disease) are identified as nontarget lesions and also are recorded at baseline. Measurements of these lesions are not required, but the presence or absence of each should be noted throughout follow-up.

Response Criteria

Evaluation of Target Lesions

The criteria have been adapted from the original WHO Handbook, taking into account the measurement of the longest diameter only for all target lesions: complete response—the disappearance of all target lesions; partial response—at least a 30% decrease in the sum of the longest diameter of target lesions, taking as reference the baseline sum longest diameter; progressive disease—at least a 20% increase in the sum of the longest diameter of target lesions, taking as reference the smallest sum longest diameter recorded since the treatment started or the appearance of one or more new lesions; stable disease—neither sufficient shrinkage to qualify for partial response nor sufficient increase to qualify for progressive disease, taking as reference the smallest sum longest diameter since the treatment started.

Evaluation of Nontarget Lesions

The criteria used to determine the objective tumor response for nontarget lesions are: complete response—the disappearance of all nontarget lesions and normalization of tumor marker level; incomplete response/stable disease—the persistence of one or more nontarget lesion(s) and/or the maintenance of tumor marker level above the normal limits; and progressive disease—the appearance of one or more new lesions and/or unequivocal progression of existing nontarget lesions.

| Target lesions | Nontarget lesions | New lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response; PR = partial response; SD = stable disease; and PD = progressive disease.

The invention claimed is:

1. A method comprising:
   (a) providing a subject sample from a subject with a neoplastic disorder wherein said subject sample has been exposed to a genotoxic anti-neoplastic agent;
   (b) determining the number of FANC D2-containing foci in said subject sample; and
   (c) comparing the number in (b) with the number of FANC D2-containing foci in a normal tissue sample that has been exposed to said genotoxic anti-neoplastic agent.

2. The method of claim 1, wherein the number of FANC D2-contaning foci is determined using an antibody specific for monoubiquitinated FANC D2.

3. The method of claim 1, wherein said exposure is less than or equal to a therapeutically effective dose.

4. The method of claim 1, wherein said exposure is at 50% or less of the therapeutically effective dose.

5. The method of claim 1, wherein said normal tissue sample is of the same type as said subject sample with said disorder.

6. The method of claim 1, wherein said subject sample is exposed to said genotoxic anti-neoplastic agent in vivo or in vitro.

7. The method of any one of the preceding claims, wherein said genotoxic anti-neoplastic agent is selected from the group consisting of 1,3-bis(2-chloroethyl) -1-nitrosourea, busulfan, carboplatin, carmustine, chlorambucil, cisplatin, cyclophosphamide, dacarbazine, daunorubicin, doxorubicin, epirubicin, etoposide, idarubicin, ifosfamide, irinotecan, lomustine, mechlorethamine, melphalan, mitomycin C, mitoxantrone, oxaliplatin, temozolomide, topotecan, and ionizing radiation.

* * * * *

UNITED STATES PATENT AND TRADEMARK OFFICE
CERTIFICATE OF CORRECTION

| | | |
|---|---|---|
| PATENT NO. | : 7,858,331 B2 | Page 1 of 1 |
| APPLICATION NO. | : 11/441289 | |
| DATED | : December 28, 2010 | |
| INVENTOR(S) | : D'Andrea et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 166 days.

Signed and Sealed this
Tenth Day of May, 2011

David J. Kappos
*Director of the United States Patent and Trademark Office*